US008361120B2

(12) United States Patent
Gabelberger et al.

(10) Patent No.: US 8,361,120 B2
(45) Date of Patent: Jan. 29, 2013

(54) OUTRIGGER

(75) Inventors: Josef Gabelberger, West Chester, PA (US); Nicholas Angert, Paoli, PA (US)

(73) Assignee: Synthes USA, LLC, Wester Chester, PA (US)

( * ) Notice: Subject to any disclaimer, the term of this patent is extended or adjusted under 35 U.S.C. 154(b) by 632 days.

(21) Appl. No.: 12/373,798

(22) PCT Filed: Jul. 27, 2007

(86) PCT No.: PCT/US2007/074633
§ 371 (c)(1),
(2), (4) Date: Mar. 8, 2010

(87) PCT Pub. No.: WO2008/014477
PCT Pub. Date: Jan. 31, 2008

(65) Prior Publication Data
US 2010/0198260 A1  Aug. 5, 2010

Related U.S. Application Data

(60) Provisional application No. 60/833,945, filed on Jul. 27, 2006, provisional application No. 60/950,809, filed on Jul. 19, 2007.

(51) Int. Cl.
*A61B 17/70* (2006.01)
(52) U.S. Cl. ........................................................ 606/264
(58) Field of Classification Search ........... 606/246–279
See application file for complete search history.

(56) References Cited

U.S. PATENT DOCUMENTS 5,047,029 A * 9/1991 Aebi et al. .................... 606/264
(Continued)

FOREIGN PATENT DOCUMENTS

DE    92 15 561.8    2/1993
JP    H11-501235    2/1999
(Continued)

OTHER PUBLICATIONS

Machine Translation of JP-H11-501235, Feb. 2, 1999.
(Continued)

*Primary Examiner* — Alvin Stewart
*Assistant Examiner* — Stuart S Bray
(74) *Attorney, Agent, or Firm* — Meunier Carlin & Curfman, LLC

(57) ABSTRACT

The present invention relates to an outrigger for securing a longitudinal spinal rod, preferably a horizontally offset spinal rod, with respect to a bone anchor. The outrigger may include a housing having a first throughbore to receive the bone anchor and a second throughbore to receive the spinal rod, a cam for surrounding the bone anchor, the cam being disposed within the first throughbore, and a collet having a passage for surrounding the spinal rod, the collet being disposed within the second throughbore. The cam may be moveable from a first position to a second position such that, in the first position, the spinal rod and bone anchor are free to move with respect to the housing and in the second position, the spinal rod and collet are secured with respect to the housing. The collet may be moveable between a first configuration to a second configuration such that movement of the cam from the first position to the second position causes the collet to move from the first configuration to the second configuration. The cam preferably may move into contact with the collet when the cam is moved into the second position. The collet preferably may be compressible into the second configuration. The cam may also include an intermediate position wherein in the intermediate position, the spinal rod is free to translate with respect to the housing but is prevented from articulating with respect thereto.

20 Claims, 17 Drawing Sheets

U.S. PATENT DOCUMENTS

| | | | |
|---|---|---|---|
| 5,312,404 A * | 5/1994 | Asher et al. | 606/264 |
| 5,344,422 A | 9/1994 | Frigg | |
| 5,501,684 A | 3/1996 | Schlapfer et al. | |
| 5,611,800 A | 3/1997 | Davis et al. | |
| 5,613,968 A | 3/1997 | Lin | |
| 5,624,441 A | 4/1997 | Sherman et al. | |
| 5,667,506 A | 9/1997 | Sutterlin | |
| 5,885,285 A | 3/1999 | Simonson | |
| 5,938,663 A * | 8/1999 | Petreto | 606/278 |
| 6,030,388 A * | 2/2000 | Yoshimi et al. | 606/278 |
| 6,187,005 B1 | 2/2001 | Brace et al. | |
| 6,626,906 B1 * | 9/2003 | Young | 606/278 |
| 6,872,208 B1 * | 3/2005 | McBride et al. | 606/86 A |
| 7,104,992 B2 * | 9/2006 | Bailey | 606/278 |
| 7,135,021 B2 * | 11/2006 | Lin | 606/264 |
| 7,166,109 B2 | 1/2007 | Biedermann et al. | |
| 7,207,992 B2 * | 4/2007 | Ritland | 606/86 A |
| 7,211,087 B2 * | 5/2007 | Young | 606/278 |
| 7,569,069 B2 * | 8/2009 | Sasing et al. | 606/250 |
| 7,744,635 B2 * | 6/2010 | Sweeney et al. | 606/264 |
| 7,803,174 B2 * | 9/2010 | Denis et al. | 606/250 |
| 2004/0092930 A1 | 5/2004 | Petit et al. | |
| 2004/0153068 A1 | 8/2004 | Janowski et al. | |
| 2004/0254574 A1 * | 12/2004 | Morrison et al. | 606/61 |
| 2005/0096654 A1 * | 5/2005 | Lin | 606/61 |
| 2005/0228382 A1 * | 10/2005 | Richelsoph et al. | 606/61 |
| 2006/0004359 A1 * | 1/2006 | Kramer et al. | 606/61 |
| 2006/0004360 A1 * | 1/2006 | Kramer et al. | 606/61 |
| 2006/0167455 A1 | 7/2006 | Clement et al. | |
| 2006/0206114 A1 * | 9/2006 | Ensign et al. | 606/61 |
| 2006/0241598 A1 * | 10/2006 | Khalili | 606/61 |
| 2006/0247624 A1 | 11/2006 | Banouskou et al. | |
| 2007/0123860 A1 * | 5/2007 | Francis et al. | 606/61 |
| 2007/0135817 A1 | 6/2007 | Ensign | |
| 2007/0161987 A1 * | 7/2007 | Capote et al. | 606/61 |
| 2007/0162006 A1 * | 7/2007 | Ritland | 606/61 |
| 2007/0173833 A1 * | 7/2007 | Butler et al. | 606/61 |
| 2008/0300633 A1 * | 12/2008 | Jackson | 606/257 |
| 2009/0118765 A1 * | 5/2009 | Mueller et al. | 606/246 |

FOREIGN PATENT DOCUMENTS

| | | |
|---|---|---|
| JP | 2002-526151 | 8/2002 |
| JP | 2004-512134 | 4/2004 |
| JP | 2006-026074 | 2/2006 |
| JP | 2007-500581 | 1/2007 |
| WO | WO 02/36026 | 5/2002 |
| WO | WO 2004/110289 | 12/2004 |
| WO | WO 2007/022790 | 3/2007 |

OTHER PUBLICATIONS

Machine Translation of JP-2002-526151, Aug. 20, 2002.
Machine Translation of JP-2004-512134, Apr. 22, 2004.
Machine Translation of JP-2006-026074, Feb. 2, 2006.
Machine Translation of JP-2007-500581, Jan. 18, 2007.
International Search Report dated Nov. 19, 2007.
"The USS Fracture System Overview" by Synthes Spine, 2001.

* cited by examiner

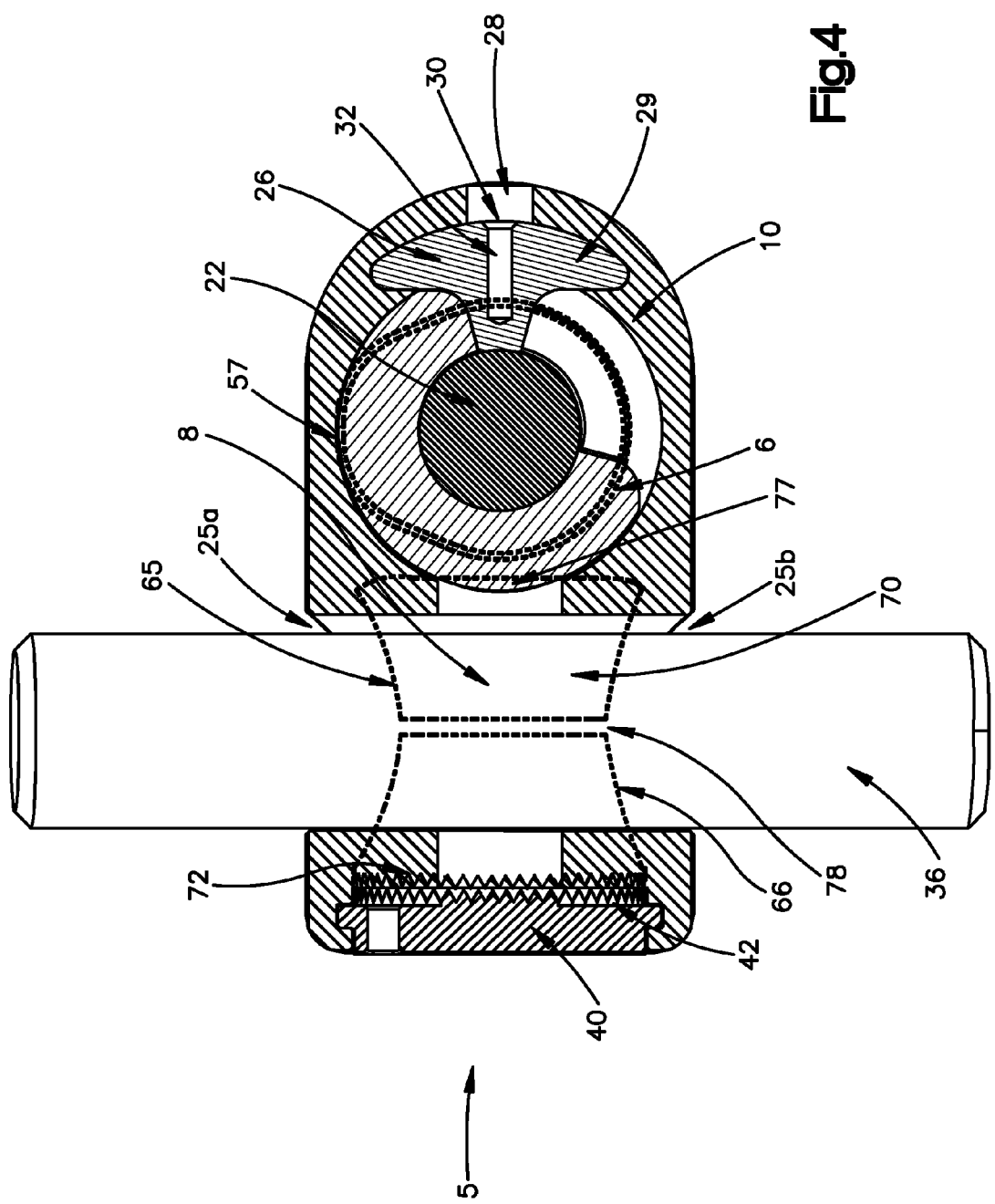

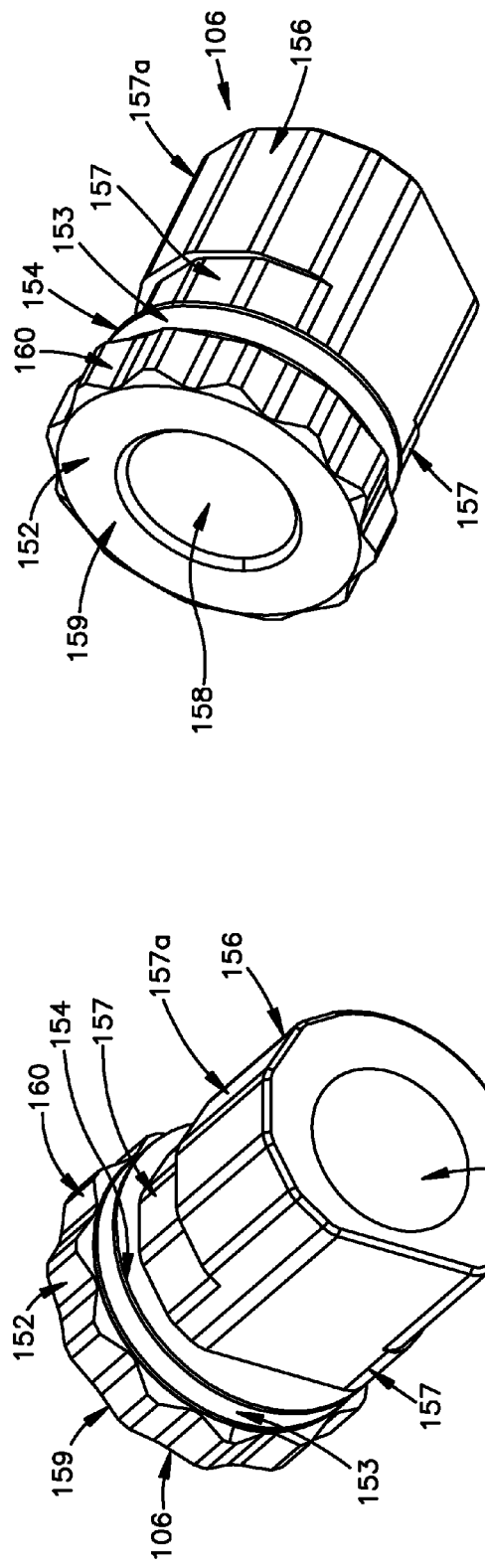
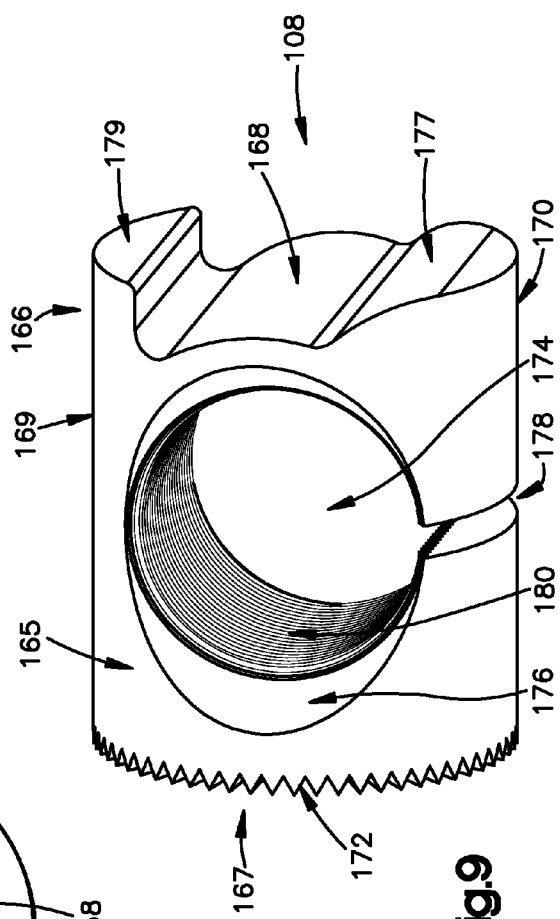
Fig.8A  Fig.8B  Fig.9

OUTRIGGER

CROSS REFERENCE TO RELATED APPLICATIONS

This application claims priority to U.S. provisional patent application Ser. No. 60/833,945, filed Jul. 27, 2006 and to U.S. provisional patent application Ser. No. 60/950,809, filed Jul. 19, 2007. The content of these applications is hereby incorporated by reference in their entirety.

FIELD OF THE INVENTION

The present invention relates to a clamping device, and, more particularly, to an outrigger for simultaneously securing all degrees of freedom of a bone anchor with respect to a longitudinal spinal rod, such that the rod may be secured at a position offset from the bone anchor.

BACKGROUND OF THE INVENTION

Spinal fusion is a procedure that involves joining two or more adjacent vertebrae with a bone fixation device to restrict movement of the vertebra with respect to one another. For a number of known reasons, spinal fixation devices are used in spine surgery to align and/or fix a desired relationship between adjacent vertebral bodies. Such devices typically include a spinal fixation element, such as, for example, a relatively rigid fixation rod, a dynamic or flexible spinal rod, etc., that is coupled to adjacent vertebrae by attaching the spinal fixation element to various bone fixation elements, such as, for example, hooks, bolts, wires, screws, etc. The bone fixation elements may commonly include heads with channels in which the spinal fixation element is inserted and subsequently clamped by a set screw or closure cap. Surgeons may commonly choose to install multiple bone fixation elements, as well as multiple spinal fixation elements, to treat a given spinal disorder. The spinal fixation elements may have a predetermined contour, and once installed, the spinal fixation element may hold the vertebrae in a desired spatial relationship, either until desired healing or spinal fusion has taken place, or for some longer period of time.

Surgeons have often encountered difficulty installing such devices because of trouble aligning the spinal fixation element(s) with the channels in the heads of the bone fixation elements. For example, the heads of bone fixation elements may often be out of vertical and/or horizontal alignment with one another because of the curvature of the spine or the size and shape of each vertebra.

The process of positioning and setting known bone fixation elements may be tedious and relatively time-consuming, typically requiring more than one surgical tool to clamp the spinal fixation elements and the bone fixation elements in desired positions. Even with a high degree of skill and care, the process of positioning an assembly of known bone fixation elements and spinal fixation elements, and clamping said bone and spinal fixation elements in place can take more time than desired during a surgical procedure, and may even result in spinal fixation elements, bone fixation elements, or both moving out of position before clamping is completed.

Thus, it is desirable to have a spinal fixation device that can secure spinal fixation elements and bone fixation elements in place with a minimum amount of time and a minimal number of surgical tools. It is also desirable to have a spinal fixation device that can secure a spinal fixation element at an axis that is offset from the axis of the bone fixation element.

SUMMARY OF THE INVENTION

The present invention is directed to an outrigger for securing a longitudinal spinal rod, preferably a horizontally offset longitudinal spinal rod, with respect to a bone anchor. In one embodiment, the outrigger may include a housing having a first throughbore or channel sized and configured to receive at least a portion of the bone anchor and a second throughbore or channel sized and configured to receive at least a portion of the spinal rod, a cam having a bore sized and configured to surround a portion of the bone anchor, the cam being at least partially disposed within the first throughbore or channel, and a collet having a passage sized and configured to surround at least a portion of the spinal rod, the collet being at least partially disposed within the second throughbore or channel. The cam preferably being moveable, more preferably rotatable, from a first position to a second position such that, in the first position, the spinal rod and bone anchor are free to move with respect to the housing and in the second position, the spinal rod and the bone anchor are secured with respect to the housing.

In an alternate embodiment, the outrigger may include a housing having a first throughbore or channel sized and configured to receive at least a portion of the bone anchor and a second throughbore or channel sized and configured to receive at least a portion of the spinal rod, a cam having a bore sized and configured to surround at least some portion of the bone anchor, the cam being at least partially disposed within the first throughbore or channel, and a collet having a passage sized and configured to surround at least a portion of the spinal rod, the collet being disposed at least partially within the second throughbore or channel. The cam preferably being moveable, more preferably rotatable, from a first position to a second position such that, in the first position, the cam does not contact and/or engage the collet and, in the second position, the cam contacts and/or engages the collet resulting in the collet moving to a second configuration from a first configuration.

In yet another alternate embodiment, the outrigger may include a collet sized and configured to permit movement of a longitudinal spinal rod when in a first configuration and to prevent movement of the longitudinal spinal rod when in a second configuration; a cam sized and configured to cause the collet to transition from the first configuration to the second configuration in response to movement of the cam, and a housing sized and configured to receive at least a portion of the collet and the cam. The cam may be an eccentric cam.

Preferably, the second throughbore or channel is substantially transverse to the first throughbore or channel and the first throughbore or channel is separated from the second throughbore or channel by a distance A.

Moreover, the cam preferably includes at least one lobe formed thereon and the collet includes at least one protrusion formed thereon, the lobe being sized and configured to contact and/or engage the protrusion when the cam is moved from the first position to the second position. The outrigger may also include an end member. The end member preferably having a roughened surface, such as for example, a toothed surface, a grooved surface, etc. for engaging a roughened surface formed on the collet when the cam is moved from the first position to the second position. The lobe contacting and/or engaging the protrusion preferably causes the roughened surface formed on the collet to contact and/or engage the roughened surface formed on the end member.

Movement of the cam preferably causes the cam to contact the collet, which in turn preferably causes the collet to compress around at least some portion of the spinal rod thereby fixing the position of the spinal rod with respect to the housing.

The collet is preferably moveable between a first configuration and a second configuration, the collet being compressed in the second configuration. The collet preferably including a slot formed therein, the slot extending from a first side to a second side thereof, the slot being in communication with the passage thus facilitating the collet being compressible. Movement of the cam from the first position to the second position preferably causes the cam to contact the collet, which in turn preferably causes the collet to move from the first configuration to the second configuration thereby fixing the position of the spinal rod with respect to the housing.

The housing may also include a lateral opening formed in a side thereof for receiving at least a portion of the collet, and an end member securable to the housing for closing at least a portion of the lateral opening. The end member may include a roughened surface for engaging a roughened surface formed on the collet.

The outrigger may also include a key or key-type arrangement, the key preferably limiting the orientation of the cam with respect to the housing. The key may be in the form of a plate having a hole and a pin, the pin being sized and configured to pass through a bore formed in the housing, through the plate and into an elongated slot formed in the cam. Rotation of the cam with respect to the housing is preferably limited by the pin and/or key contacting the slot formed in the cam.

Preferably, the cam moves from the first position to the second position upon rotation of the cam by a surgical tool. More preferably, the cam moves from the first position to the second position by rotation of the surgical tool through an angle of less than 360 degrees.

Moreover, movement of the cam from the first position to the second position preferably causes the bone anchor to contact the housing thereby fixing the position of the bone anchor with respect to the housing.

The cam may also be moveable to an intermediate position wherein the spinal rod is free to translate with respect to the housing (e.g. movement of the rod, with respect to the housing, substantially parallel with the longitudinal axis of the rod) but is prevented from articulating (e.g. pivoting of the rod, with respect to the housing, about a longitudinal axis that is substantially parallel with the longitudinal axis of the second throughbore) and/or rotating (e.g. rotation of the rod, with respect to the housing, about an axis that is parallel to the longitudinal axis of the rod). The cam may include a first lobe and a second lobe, wherein movement of the cam from the first position to the intermediate position may cause the first lobe to contact the collet. Movement of the cam from the intermediate position to the second position may cause the second lobe to contact the collet. The collet preferably including a first protrusion and a second protrusion, the first protrusion being sized and configured to contact the first lobe and the second protrusion being sized and configured to contact the second lobe. Movement of the cam from the first position to the intermediate position may cause the first lobe to contact the first protrusion which, in turn, may cause the collet to engage an end member. Movement of the cam from the intermediate position to the second position may cause the second lobe to contact the second protrusion which, in turn, may cause the collet to compress around some portion of the spinal rod.

BRIEF DESCRIPTION OF THE DRAWINGS

The system is explained in even greater detail in the following exemplary drawings. The drawings are merely exemplary to illustrate the structure of preferred devices and certain features that may be used singularly or in combination with other features. The claims should not be limited to the embodiments shown.

FIG. 4 is a bottom cross-sectional view of the outrigger of FIG. 1 in a first position;

FIG. 8A is a perspective view of a cam that may be used in connection with the outrigger shown in FIG. 7;

FIG. 8B is an alternate perspective view of the cam shown in FIG. 8A;

FIG. 9 is a perspective view of a collet that may be used in connection with the outrigger shown in FIG. 7;

DETAILED DESCRIPTION

Certain exemplary embodiments will now be described with reference to the drawings. In general, such embodiments relate to a clamping device or an outrigger (collectively referred to herein as an outrigger), by way of non-limiting example, an outrigger for use in securing a bone anchor with respect to a longitudinal spinal rod in a posterior spinal fixation. The invention may have other applications and uses and should not be limited to the structure or use described and illustrated. As will be described in greater detail below, the outrigger may include a cam, a collet and a housing.

Moreover, while the outrigger will be described as and may generally be used in the spine (for example, in the lumbar, thoracic or cervical regions), those skilled in the art will appreciate that the outrigger may be used for fixation of other parts of the body such as, for example, joints, long bones or bones in the hand, face, feet, etc. In addition, the outrigger may be used for external fixation of the body such as, for example, where rods are joined outside of the patient's body along, for example, the patient's long bones, spine, etc. The outrigger may also be used to connect proximal or distal extensions to a rib hook in an expandable prosthetic rib, as a clamping assembly/mechanism for a transconnector (e.g., a device that connects two rods with one another during spinal surgery), to connect and secure the pieces of a retractor system, or to attach components, for example, retractor systems to a surgical table. The outrigger may be constructed from any biocompatible material known in the art including, but not limited to, stainless steel, titanium, titanium alloys, etc.

Figure 1:
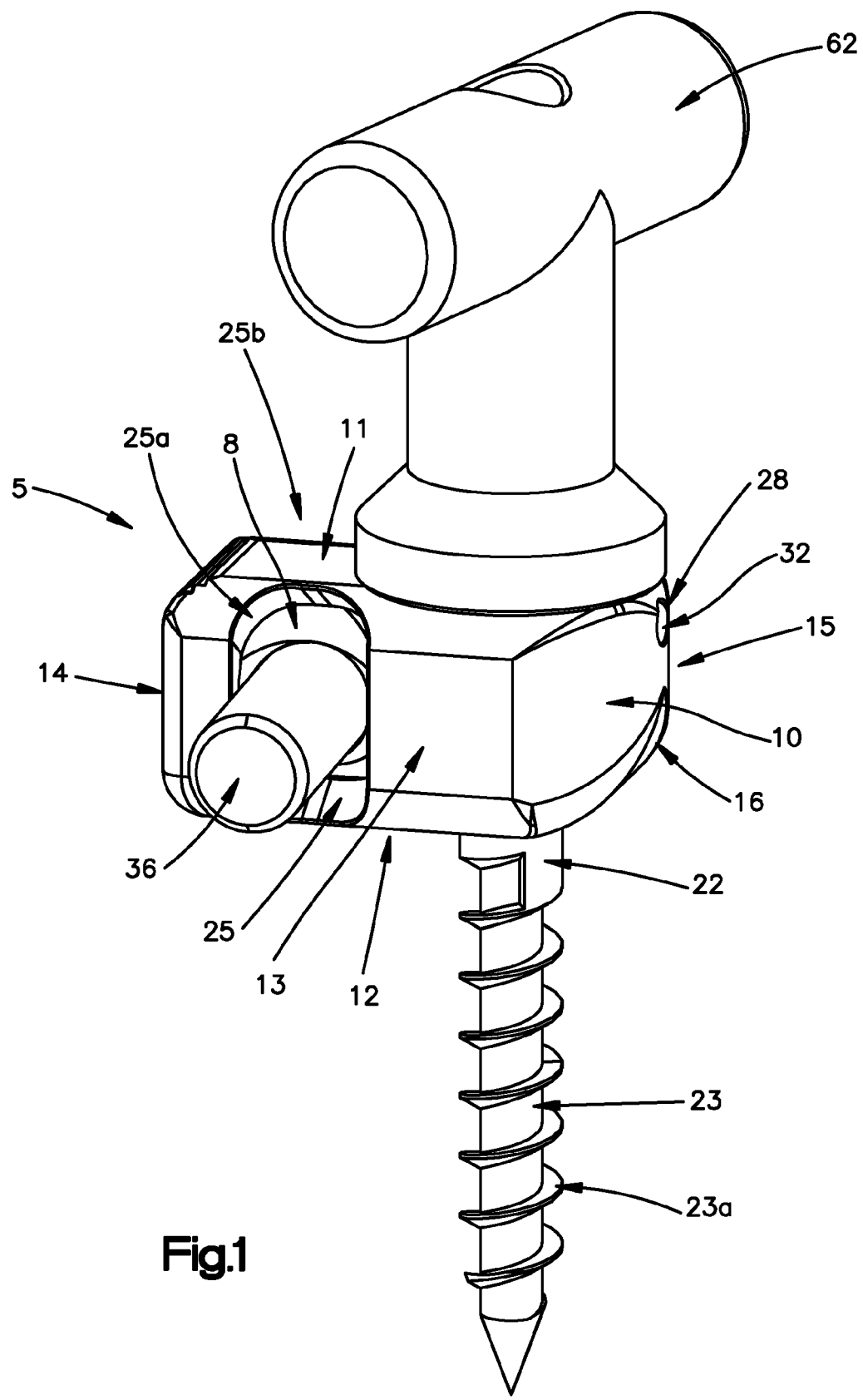
FIG. 1 is a perspective view of an exemplary embodiment of an outrigger.
Figure 1A:
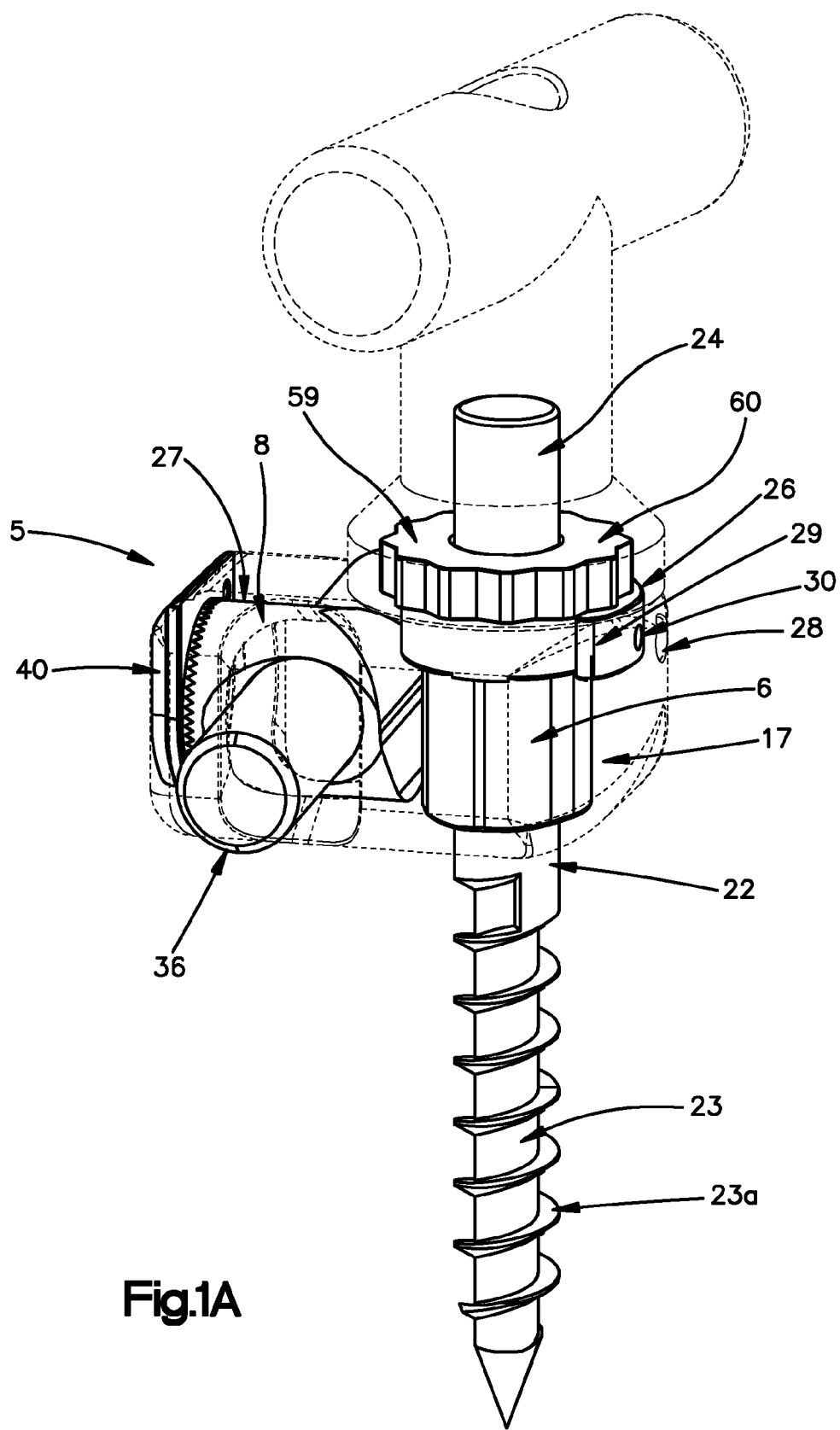
FIG. 1A is another perspective view of the outrigger of FIG. 1 with parts in phantom to show the internal components.
Figure 2:
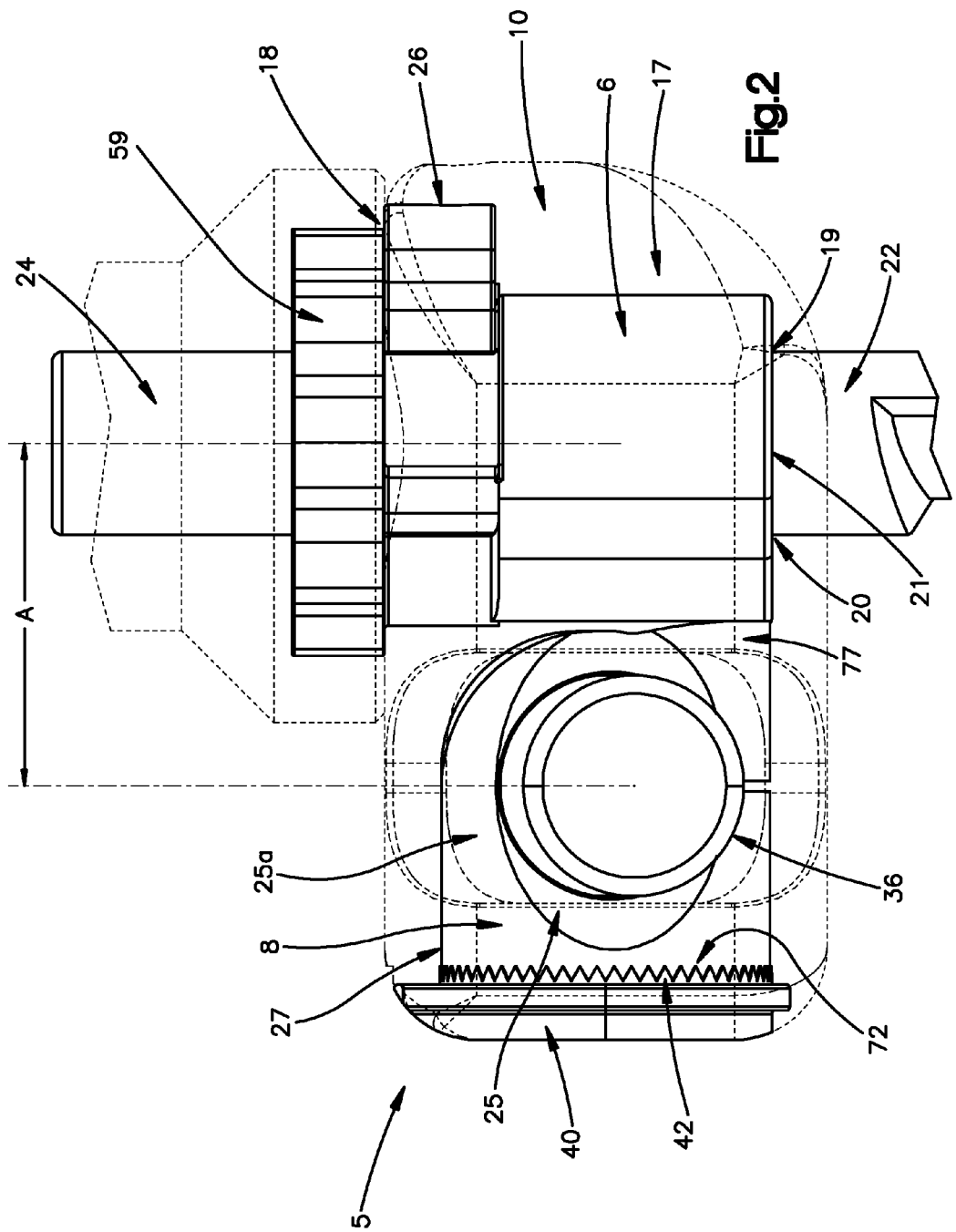
FIG. 2 is a side view of the outrigger of FIG. 1 with parts in phantom to show the internal components.

As shown in FIGS. 1, 1A and 2, the outrigger 5 may include a cam 6, a collet 8 and a housing 10 for interconnecting a bone anchor 22, and hence a vertebra, to a longitudinal spinal rod 36.

As generally understood by one of ordinary skill in the art, it should be understood that the longitudinal spinal rod 36 may include, but not be limited to, a solid rod, a non-solid rod, a flexible or dynamic rod, etc. It should be understood that the outrigger is not limited in use to any particular type of longitudinal spinal rod 36.

The bone anchor 22 may include a bone engaging portion 23 and a shaft portion 24. As shown, the bone engaging portion 23 may include threads 23a for threadably engaging the targeted vertebra. As generally known by one of ordinary skill in the art, the bone engaging portion 23 may be in other forms, such as, for example, a hook, an implant, a wire, etc. It should be understood that the outrigger is not limited in use to any particular type of bone anchor 22.

As shown, the housing 10 may include a top end 11, a bottom end 12, a first side 13, a second side 14, a third side 15, and a fourth side 16 so that the housing 10 may be generally in the form of a rectangular body. However, those skilled in the art will recognize that the housing 10 may be in the form of any number of shapes, for example, square, ellipsoid, spherical, etc. It should be understood that the outrigger 5 is not to be limited by the shape of the housing 10.

The housing 10 may also include an inner cavity 17, a top hole 18 and a bottom hole 20, the top and bottom holes 18, 20 preferably being in communication with the inner cavity 17 to define a first throughbore or channel 21 (collectively referred to herein as the first throughbore), which extends from the top end 11 to the bottom end 12. The first throughbore 21 may be sized and configured to receive at least some portion of the shaft portion 24 of the bone anchor 22. Moreover, the first throughbore 21 may also be sized and configured to receive at least some portion of and preferably the entire cam 6, the cam 6 preferably being disposed around at least some portion of the shaft portion 24 of the bone anchor 22, as will be described in greater detail below. More preferably, the top hole 18 may be sized and configured to receive the cam 6, while the bottom hole 20 may be sized and configured to prevent the cam 6 from exiting the housing 10 through the bottom hole 20. Thus, in essence, the configuration of the housing 10 acts as a stop to prevent the cam 6 from exiting through the bottom end 12 of the housing 10. Moreover, the configuration of the housing 10 and cam 6 creates an area of contact 19 between the bone anchor 22 and the housing 10, as will be described in greater detail below.

The housing 10 may also include a first lateral opening 25a formed in the first side 13 and a second lateral opening 25b formed in the third side 15, the first and second lateral openings 25a, 25b preferably being in communication with the inner cavity 17 to define a second throughbore or channel 25 (collectively referred to herein as the second throughbore) for receiving at least some portion of the longitudinal spinal rod 36. As shown, the second throughbore 25 is preferably oriented substantially transverse with respect to the first throughbore 21. Moreover, preferably, the longitudinal axis of the second throughbore 25 is separated by a distance A from the centerline of the first throughbore 21 so that the longitudinal spinal rod 36 can be offset from the bone anchor 22. The distance "A" may be from about 5 mm to about 50 mm, preferably from about 8 mm to about 25 mm. As will be generally understood by one of ordinary skill in the art, the size of the offset may depend on the region of the body where the outrigger is being implanted. For example, the distance A may be larger in the lumbar region of the spine as compared to the cervical region of the spine. It should be understood that the outrigger is not limited to any particular dimensions.

The housing 10 may also include a third opening 27 formed in either of the second side 14 or the fourth side 16 (shown here as the second side 14), the third opening 27 preferably being in communication with the inner cavity 17 to enable at least a portion of and preferably the entire collet 8 to be inserted and/or received within the inner cavity 17 of the housing 10 so that the collet 8 can be disposed around at least some portion of the spinal rod 36, as will be described in greater detail below.

The housing 10 may also include a key or key type arrangement 26 between the cam 6 and the housing 10 so that, once inserted, the key 26 prevents the cam 6 from exiting the housing 10 through the top hole 18 formed in the housing 10. Moreover, as previously mentioned, the configuration of the housing 10 acts as a stop to prevent the cam 6 from exiting the housing 10 via the bottom hole 20, thus between the configuration of the housing 10 and the key 26, the cam 6 is preferably secured within the housing 10 between the top and bottom ends 11, 12. The key 26 preferably also permits the cam 6 to be inserted into the housing 10 only when it is properly oriented, as will be described in greater detail below. Moreover, preferably the key 26 may act to limit the rotational movement of the cam 6, as will be discussed in greater detail below. As generally understood by one of ordinary skill in the art, any key or key-type arrangement 26 may be used. For example, one of the cam 6 and housing 10 may include a projection for engaging a groove formed on the other of the cam 6 or housing 10. The key 26 may be integrally formed with the housing 10, or may be a separate and independent piece and attached thereto. Other examples would include forming the cam 6 and housing 10 so that the cam 6 has an asymmetrical or unique shape and the housing 10 has an opening corresponding to the asymmetrical or unique shape of the cam 6.

As shown, the key 26 is preferably in the form of a plate 29 and a pin 32. The first throughbore 21 formed in the housing 10 is preferably sized and configured to receive the plate 29 adjacent to the cam 6, preferably after the cam 6 has been inserted into the housing 10. The plate 29 is preferably sized and configured to match the outer contour or circumference of the cam 6. Although described as a plate, the plate 29 may have other shapes and configurations which would not be considered a plate or plate-like. The plate 29 may be sized and configured with a hole 30. In addition, the housing 10 may include a bore 28 extending from one of the sides thereof (shown as the fourth side 16), the bore 28 being concentric with the hole 30 formed in the plate 29 so that the pin 32 can be inserted through the bore 28 formed in the housing 10 and into the hole 30 formed in the plate 29. In this manner, the cam 6 may be prevented from exiting the housing 10 through the top end 11.

The housing 10 may also include a plate-like end member 40 adjacent to the third opening 27 formed in either of the second 14 or fourth sides 16 (shown here as the second side 14), the plate-like end member 40 preferably being sized and configured to cover at least a portion and preferably the entire third opening 27 formed in the housing 10. While described as plate-like, the end member 40 may have other shapes and configurations. As shown in FIGS. 1A and 2, the end member 40 may include a roughened surface 42 for engaging the collet 8, as will be described in greater detail below. The roughened surface 42 formed on the end member 40 may be in the form of a toothed surface, a grooved surface, etc. As will be generally understood by one of ordinary skill in the art, any combination of surfaces that create increased friction to increase engagement between the collet 8 and the end member 40 when they are pressed against each other may be used.

The end member 40 may be integrally formed with the housing 10, or may be a separate and independent piece and attached thereto. If separately formed, the end member 40 may be connected to the housing 10 by any means known in the art including, but not limited to, mechanically fastening, adhesive, welding, etc. Preferably (as best shown in the alternative embodiment of FIGS. 7 and 7A, which will be discussed in greater detail below), the end member 40 may include a projection 144 extending from one or more of the sides thereof, the projection 144 being sized and configured to engage a slot 146 formed in the housing 10, for example in a tongue and groove type connection, so that the end member 40 may be slidably received within the housing 10. Moreover, the housing 10 and the end member 40 may also include concentric bores for receiving a pin 151 to further secure the end member 40 to the housing 10.

Figure 3A:
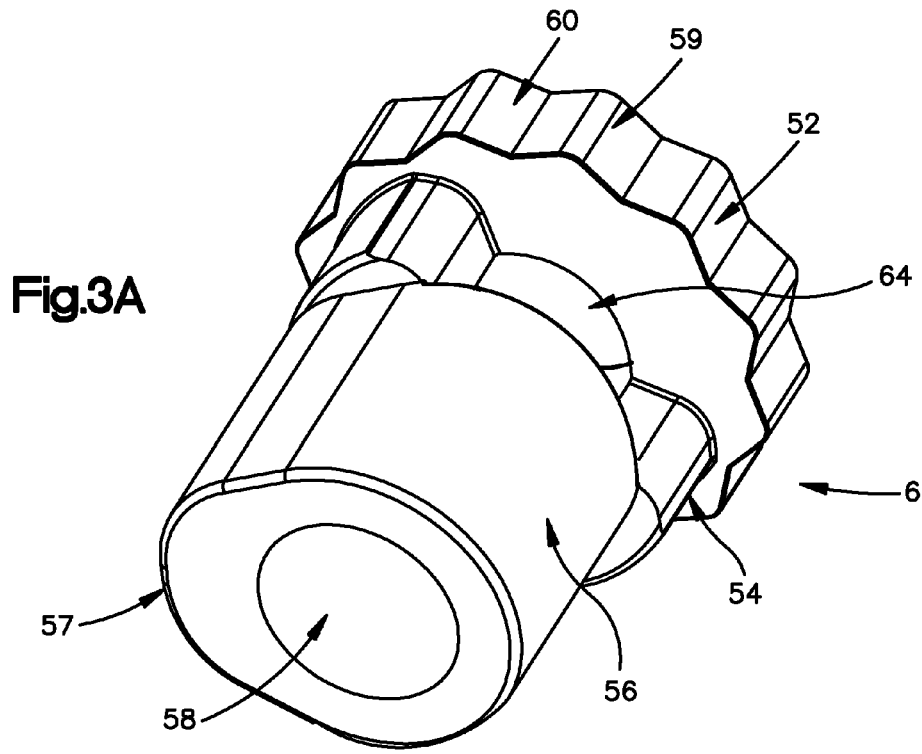
FIG. 3A is a perspective view of a cam that may be used in connection with the outrigger of FIG. 1.

As shown in FIG. 3A, the cam 6 may include a top portion 52, a middle portion 54, a bottom portion 56 and a bore 58 extending from the top portion 52 to the bottom portion 56. Preferably, the bore 58 is sized and configured to receive at least some portion of the shaft portion 24 of the bone anchor 22. The bore 58 formed in the cam 6 may be substantially smooth or alternatively may include an inner thread (not shown) to permit the bone anchor 22 to be inserted through the cam 6, the bone anchor 22 may have a bone thread that is larger than the inner diameter of the bore 58 formed in the cam 6.

The top portion 52 of the cam 6 may include a fastener engaging mechanism 59 for engaging a surgical tool to facilitate rotation of the cam 6 from a first position to a second position, as will be described in greater detail below. The fastener engaging mechanism 59 may be any mechanism known in the art including, but not limited to, a screwdriver, a ratchet, a socket, etc. As shown, the fastener engaging mechanism 59 may be a gear-shaped portion 60 sized and configured to engage a corresponding drive mechanism 62 (as best shown in FIG. 1A).

The middle portion 54 preferably includes an elongated slot 64, the elongated slot 64 being sized and configured to receive the key 26. As will be readily understood by one of ordinary skill in the art, incorporation of the elongated slot 64 and the key 26 may act to limit or control the amount of rotational movement of the cam 6 with respect to the housing 10. Preferably the elongated slot 64 is sized and configured to be wider than the key 26 to permit rotation of the cam 6 with respect to the housing 10. Rotation of the cam 6 may be limited by the key 26, preferably the pin 32, contacting the slot 64 formed in the cam 6. Preferably, the key 26 and the elongated slot 64 are sized and configured to permit the cam 6 to rotate less than 360 degrees, such as, for example, 30, 60, 145, 180, 270, etc. Although, as generally known in the art, the cam 6 may be sized and configured to rotate any number of degrees.

The bottom portion 56 of the cam 6 preferably includes a lobe 57 formed thereon. For example, when viewed from the bottom, the cam 6 has a non-circular diameter such that the radius of the cam 6 with respect to the longitudinal axis of the bore 58 varies along its perimeter. In this manner, the cam 6 is in the form of an eccentric cam. The cam 6 may include a stepped radius profile as will be described in greater detail below in connection with the dual eccentric cam.

Figure 3B:
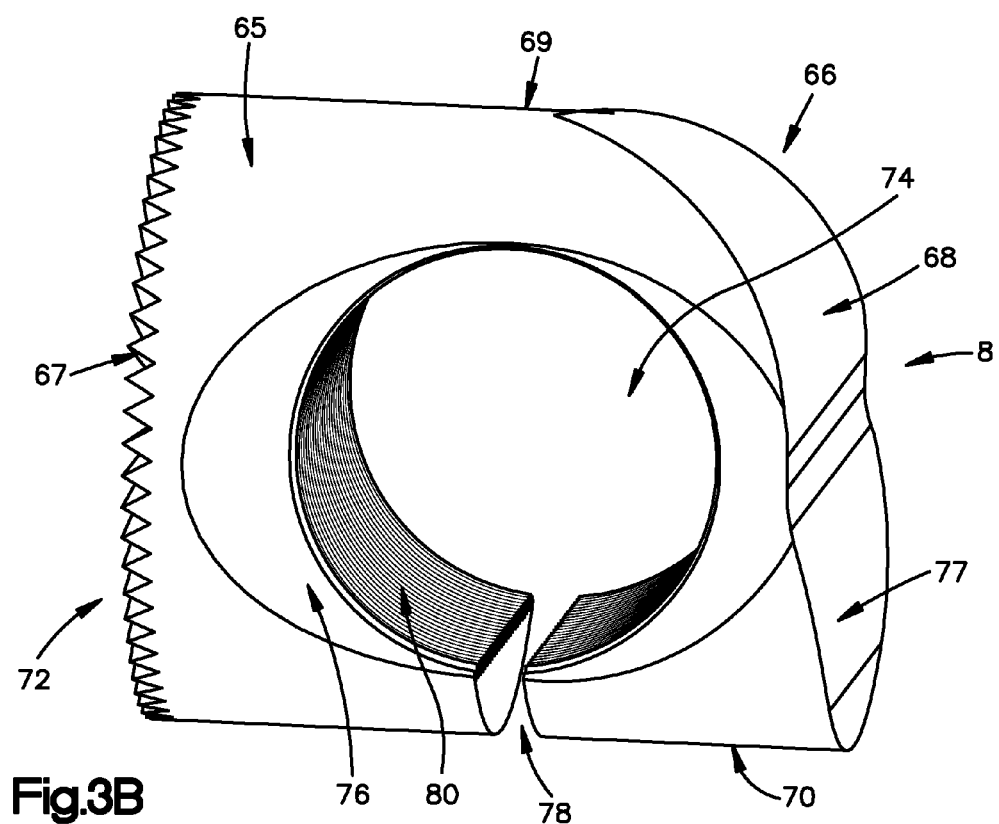
FIG. 3B is a perspective view of a collet that may be used in connection with the outrigger of FIG. 1.

As shown in FIG. 3B, the collet 8 may include a first side 65, a second side 66, a third side 67, a fourth side 68, a top side 69, a bottom side 70 and a passage 74 extending from the first side 65 to the second side 66 of the collet 8. The passage 74 is preferably sized and configured to receive at least some portion of the longitudinal spinal rod 36, and more preferably may be sized and configured so that, once the collet 8 is inserted into the housing 10 via the third opening 27, the passage 74 formed in the collet 8 may be aligned with the second throughbore 25 formed in the housing 10 so that the longitudinal spinal rod 36 may be received and/or passed through the housing 10. As shown, the first and second sides 65, 66 may include a tapered depression 76 formed thereon, the tapered depression 76 facilitating easier insertion of the spinal rod 36 through the collet 8. Angular movement of the longitudinal spinal rod 36 with respect to the housing 10 is enabled through articulation of the outer, preferably cylindrical, surface of the collet 8 contacting the inner surface of the second throughbore 25 formed in the housing 10. Alternatively, for example, the spinal rod 36 and collet 8 may be formed as one piece so that only articulation of the spinal rod 36 with respect to the housing 10 and/or bone anchor 22 is permitted (e.g., no rotation and/or translational movement of the collet 8 with respect to the spinal rod 36 will be permitted).

As shown, one of the third or fourth sides 67, 68 (shown as the fourth side 68) may include a surface for contacting the cam 6, preferably a protrusion 77 formed on the collet 8 for contacting the lobe 57 formed on the cam 6, while the other of the third or fourth sides 67, 68 (shown as the third side 67) may include a roughened surface 72 for contacting the roughened surface 42 formed on the end member 40. As previously mentioned, the roughened surface 72 formed on the collet 8 may be in the form of a toothed surface, a grooved surface, etc. As will be generally understood by one of ordinary skill in the art, any combination of surfaces that create increased friction to increase engagement between the collet 8 and the end member 40 when they are pressed against each other may be used. More preferably, as shown, the collet 8 may include a projection 77 for contacting the lobe 57 formed on the bottom portion 56 of the cam 6 such that rotation of the cam 6 preferably causes the lobe 57 to contact and/or engage the protrusion 77 formed on the collet 8, which in turn preferably causes the roughened surface 72 formed on the collet 8 to contact and/or engage the roughened surface 42 formed on the end member 40.

Moreover, as shown, the bottom side 70 of the collet 8 may include a slot 78 formed therein, the slot 78 preferably extending from the first side 65 to the second side 66. The slot 78 also preferably may be in communication with the passage 74 so that, as generally understood by one of ordinary skill in the art, the collet 8 is compressible. In its natural state, the collet 8 is preferably sized and configured in a first configuration such that the longitudinal spinal rod 36 may move (e.g., translate, rotate, articulate, etc.) within the passage 74. Thereafter, application of a force, for example by rotation of the cam 6, preferably causes the collet 8 to move to a second configuration wherein the longitudinal spinal rod 36 is substantially prevented from any movement (e.g., translation, rotation, articulation, etc.) within the passage 74. Rotation of the cam 6 preferably causes the lobe 57 to contact and/or engage the collet 8, which in turn preferably causes the collet 8 to compress around at least some portion of the spinal rod 36 thereby fixing the position of the spinal rod 36 with respect to the housing 10. By way of example, translation means movement of the spinal rod, with respect to the housing, substantially parallel with the longitudinal axis of the spinal rod, articulation means pivoting of the spinal rod, with respect to the housing, about an axis that is generally parallel with the longitudinal axis of the second throughbore and rotation means rotation of the spinal rod, with respect to the housing, about an axis that is parallel to the longitudinal axis of the rod. As shown, the passage 74 may include a threaded, serrated or roughened surface 80 to further help prevent movement of the longitudinal spinal rod 36 when the collet 8 is in the second configuration. It should be noted that the collet 8 can be made compressible by any other means known in the art including, but not limited to, a plurality of slots, weakened areas, etc.

In use, the outrigger 5 may be pre-assembled by the manufacturer and/or surgeon so that the cam 6 and the collet 8 are secured within the housing 10. Next, the longitudinal spinal rod 36 may be passed through the second throughbore 25 formed in the housing 10 and the passage 74 formed in the collet 8. The outrigger 5 may then be connected to the bone anchors 22 that may have been previously secured to a patient's bone, for example, a vertebra. The shaft portion 24 of the bone anchor 22 may be received by the first throughbore 24 of the housing 10 and by the bore 58 formed in the cam 6. Alternatively, as will be generally understood by one of ordinary skill in the art, the outrigger 5 may be secured to the bone anchor 22 prior to the bone anchors 22 being secured to the patient's bone. Moreover, the outrigger 5 and bone anchors 22 may be secured to the patient's bone prior to the spinal rod 36 being inserted into the second throughbore 25 of the housing 10 and the passage 74 formed in the collet 8.

Figure 5:
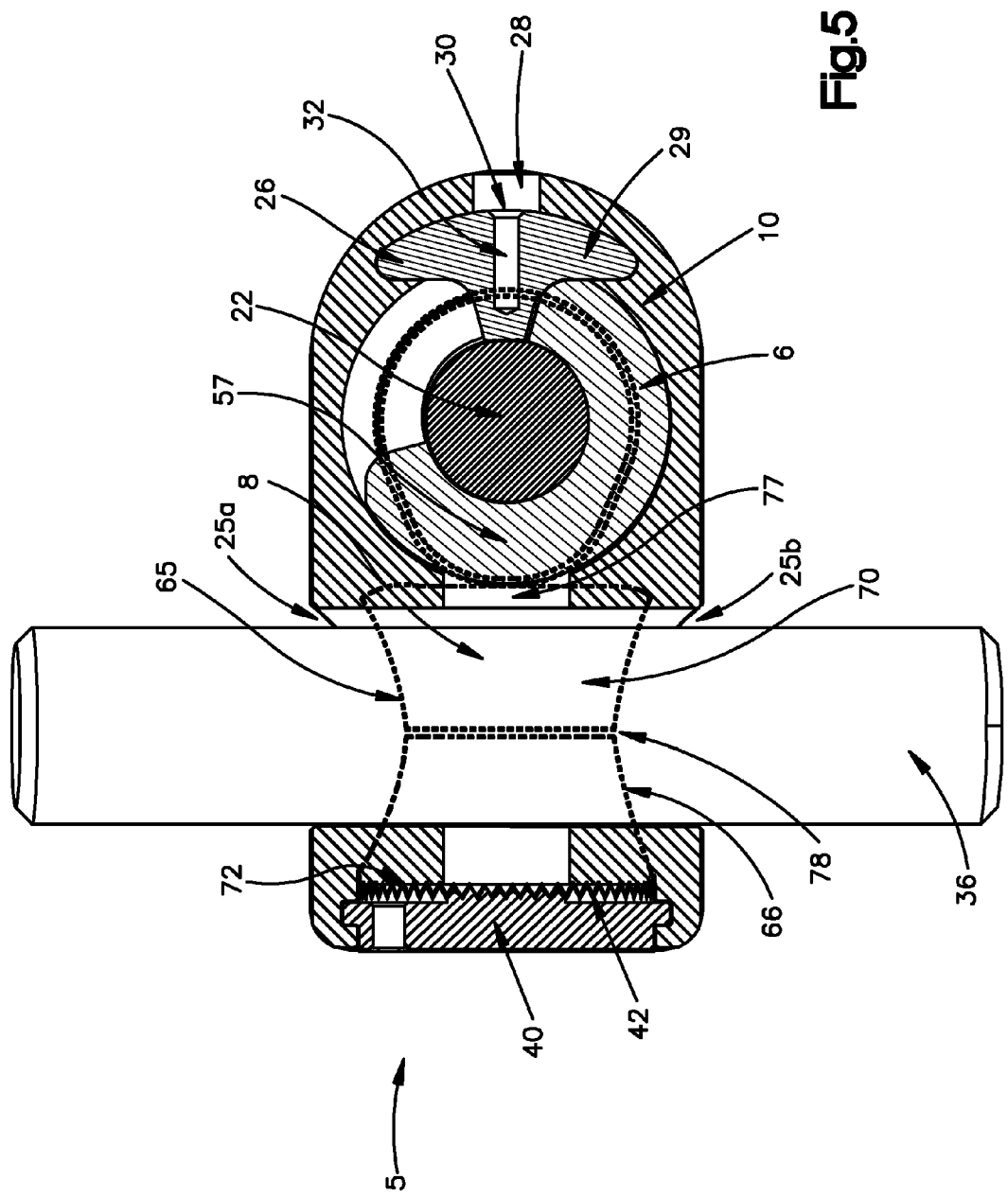
FIG. 5 is a bottom cross-sectional view of the outrigger of FIG. 1 in a second position.

As best shown in FIG. 4, the cam 6 is positioned in the housing 10 in a first position whereby the cam 6 preferably does not contact and/or engage the collet 8 so that the collet 8 preferably may be in the first configuration and the collet 8 does not contact and/or engage the end member 40. In this position, the longitudinal spinal rod 36 may freely move with respect to the housing 10 and the bone anchor 22 may freely move with respect to the housing 10. Once the desired position has been achieved, the surgeon may use a surgical tool, such as the drive mechanism 62, to engage the fastener engaging mechanism 59 formed on the top portion 52 of the cam 6. Thereafter, as best shown in FIG. 5, rotation of the surgical tool preferably causes the cam 6 to rotate, which in turn preferably causes the cam 6 to contact and/or engage the collet 8, which in turn preferably causes the collet 8 to contact and/or engage the end member 40. In addition, rotation of the cam 6 preferably causes the collet 8 to move and/or transition from its first configuration, wherein the spinal rod 36 is free to move with respect to the house 10, to its second configuration, wherein the spinal rod 36 is substantially prevented from moving with respect to the housing 10.

More specifically, preferably, rotation of the surgical tool causes the cam 8 to rotate, which in turn preferably causes the lobe 57 formed on the cam 8 to contact and/or engage the protrusion 77 formed on the collet 8, which in turn preferably causes the collet 8 to compress around some portion of the spinal rod 36 and further preferably causes the roughened surface 72 formed on the collet 8 to contact and/or engage the roughened surface 42 formed on the end member 40. In this manner, the collet 8 may become rotationally secure with respect to the end member 40, in addition to tightening around some portion of the longitudinal spinal rod 36, thereby preventing further movement (i.e., rotation, translation, articulation, etc.) of the longitudinal spinal rod 36.

Figure 6:
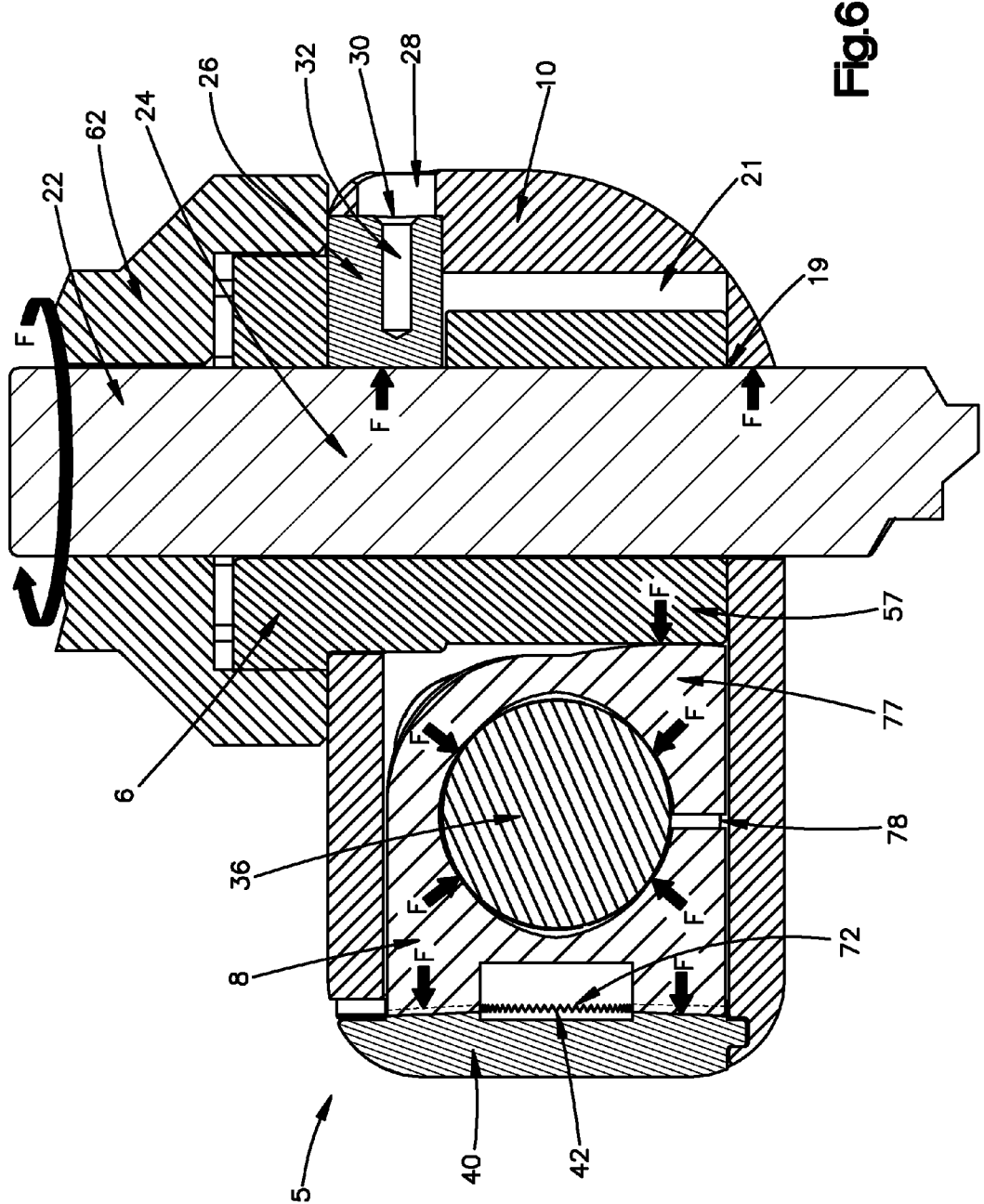
FIG. 6 is a cross-sectional view of the outrigger of FIG. 1 showing the forces operating on the outrigger as the outrigger is moved from the first position to the second position.

Additionally, as shown in FIG. 6, the application of force on the collet 8 by the cam 6 may result in a force of equal magnitude and opposite direction being applied to the cam 6, which in turn applies an equal force to the bone anchor 22. In this manner, the shaft portion 24 of the bone anchor 22 may be biased against the housing 10, for example, in the area 19 of the housing 10 below the cam 6 thereby securing the bone anchor 22 with respect to the housing 10. In addition, the shaft portion 24 of the bone anchor 22 may be biased against the key 26, thereby further securing the bone anchor 22 with respect to the housing 10.

Similar to the outrigger 5 described above, the outrigger 105, as shown in FIGS. 7-15, may include a cam 106, a collet 108 and a housing 110 for interconnecting a bone anchor 22, and hence a vertebra, to a longitudinal spinal rod 36. As previously mentioned, the outrigger is not limited in use to any particular type of longitudinal spinal rod 36 or bone anchor 22.

Similar to the housing 10 described above, the housing 110 may include a top end 111, a bottom end 112, a first side 113, a second side 114, a third side 115, and a fourth side 116 so that the housing 110 may be generally in the form of a rectangular body. However, as previously mentioned, the outrigger 105 is not limited to any particular shape for the housing 110.

The housing 110 may also include an inner cavity 117, a top hole 118 and a bottom hole 120, the top and bottom holes 118, 120 preferably being in communication with the inner cavity 117 to define a first throughbore 121, which extends from the top end 111 to the bottom end 112. The first throughbore 121 may be sized and configured to receive at least some portion of the shaft portion 24 of the bone anchor 22. Moreover, the first throughbore 121 may also be sized and configured to receive at least a portion of, and preferably the entire cam 106, the cam 106 preferably being at least partially disposed around some portion of the shaft portion 24 of the bone anchor 22. More preferably, the top hole 118 may be sized and configured to receive the cam 106, while the bottom hole 120 may be sized and configured to prevent the cam 106 from exiting the housing 110 through the bottom hole 120. Thus, in essence, the bottom end 112 may act as a stop to retain the cam 106 within the housing 110.

The housing 110 may also include a first lateral opening 125a formed in the first side 113 and a second lateral opening 125b formed in the third side 115, the first and second lateral openings 125a, 125b preferably being in communication with the inner cavity 117 to define a second throughbore 125 for receiving at least a portion of the longitudinal spinal rod 36. As shown, the second throughbore 125 is preferably oriented substantially transverse with respect to the first throughbore 121. Moreover, preferably, the longitudinal axis of the second throughbore 125 is separated by the distance "A" from the centerline of the first throughbore 121 so that the longitudinal spinal rod 36 can be offset from the bone anchor 22.

The housing 110 may also include a third opening 127 formed in either of the second side 114 or the fourth side 116 (shown here as the second side 114), the third opening 127 preferably being in communication with the inner cavity 117 to enable the collet 108 to be inserted and/or received within the inner cavity 117 of the housing 110 so that the collet 108 can be at least partially disposed around some portion of the spinal rod 36.

The housing 110 may also include a key or key type arrangement 126 between the cam 106 and the housing 110 so that, once inserted, the key 126 prevents the cam 106 from exiting the housing 110 through the top hole 118 formed in the housing 110. Moreover, as previously mentioned, the configuration of the housing 110 acts as a stop to prevent the cam 106 from exiting the housing 110 via the bottom end 112, thus between the configuration of the housing 110 and the key 126, the cam 106 is preferably secured within the housing 110. Moreover, preferably the key 126 may act to limit the rotational movement of the cam 106, as will be described in greater detail below. As generally understood by one of ordinary skill in the art and as previously mentioned, any key or key-type arrangement may be used.

Figure 7:
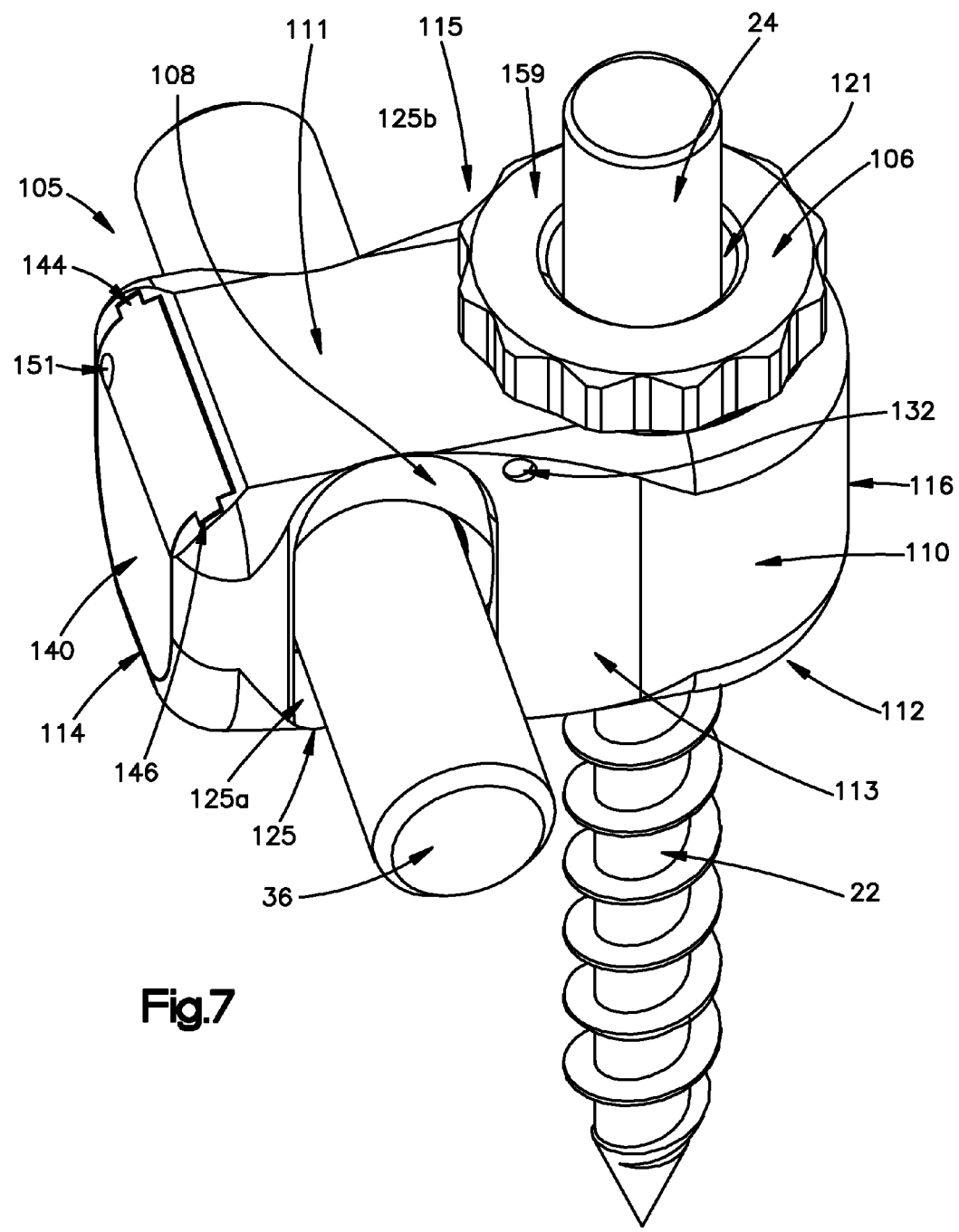
FIG. 7 is a perspective view of an alternative embodiment of the outrigger.
Figure 7A:
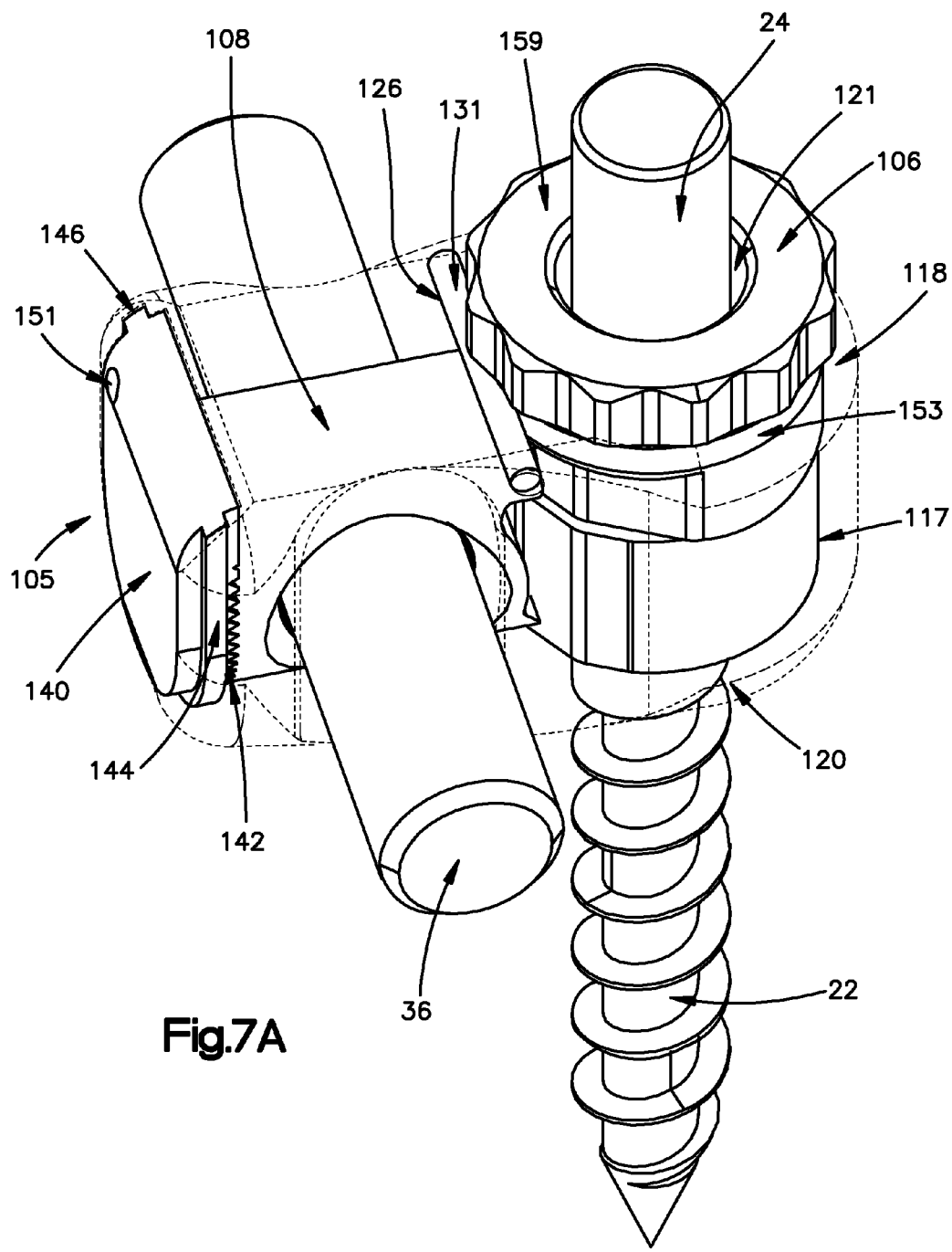
FIG. 7A is another perspective view of the outrigger of FIG. 7, with parts in phantom to show the internal components.

As best shown in FIG. 7A, the key 126 may be in the form of a dowel rod 131 that is preferably insertable into a groove 153 formed in the cam 106. The housing 110 may include one or more lateral bores 132 for receiving one or more dowel rods 131. As shown, the bore 132 preferably extends from the first side 113 to the third side 115. Once inserted, the dowel rod 131 may engage the groove 153 formed in the cam 106, thereby preventing the cam 106 from exiting the housing 110 through the top end 111 of the housing 110.

Figure 10:
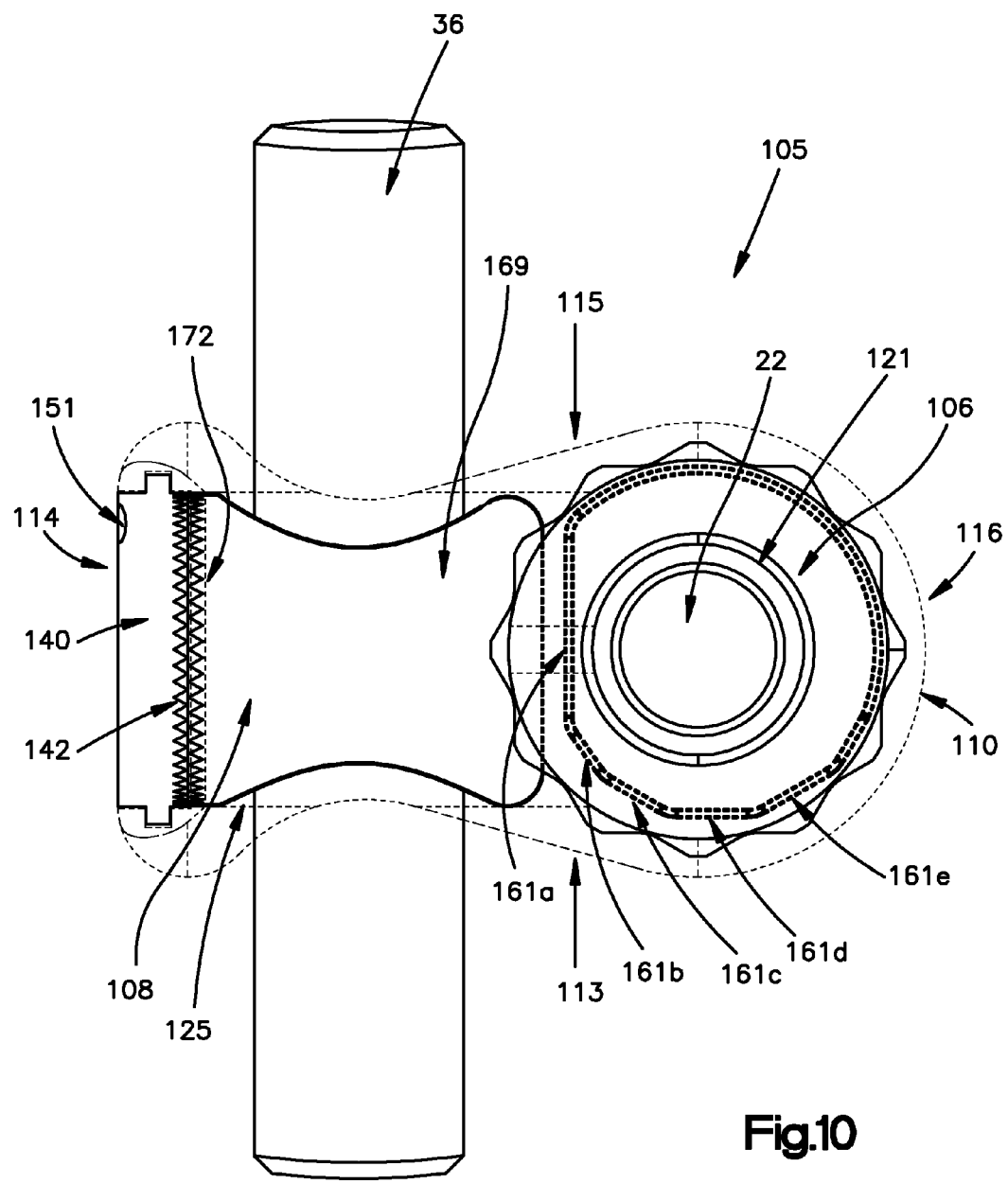
FIG. 10 is a top view of the outrigger shown in FIG. 7 in a first position, with parts in phantom to show the internal components.

The housing 110 may also include a plate-like end member 140 adjacent to the third opening 127 formed in either of the second 114 or fourth sides 116 (shown here as the second side 114), the plate-like end member 140 preferably being sized and configured to cover at least a portion and preferably the entire third opening 127 formed in the housing 110. While described as plate-like, the end member 140 may have other shapes and configurations. As shown in FIGS. 7A and 10, the end member 140 may include a roughened surface 142 for engaging the collet 108, as will be described in greater detail below. The end member 140 may be integrally formed with the housing 110, or may be a separate and independent piece and attached thereto. If separately formed, the end member 140 may be connected to the housing 110 by any means known in the art including, but not limited to, mechanically fastening, adhesive, welding, etc. As best shown in FIGS. 7 and 7A, preferably the end member 140 may include a projection 144 extending from one or more of the sides thereof, the projection 144 being sized and configured to engage a slot 146 formed in the housing 110, for example in a tongue and groove type connection, so that the end member 140 may be slidably received within the housing 110. Moreover, the housing 110 and the end member 140 may also include concentric bores for receiving a pin 151 to further secure the end member 140 to the housing 110.

As shown in FIGS. 8A and 8B, the cam 106 may include a top portion 152, a middle portion 154, a bottom portion 156 and a bore 158 extending from the top portion 152 to the bottom portion 156. Preferably, the bore 158 is sized and configured to receive at least some portion of the shaft portion 24 of the bone anchor 22. The bore 158 formed in the cam 106 may be substantially smooth or alternatively may include an inner thread (not shown) to permit the bone anchor 22 to be inserted through the cam 106, the bone anchor 22 may have a bone thread that is larger than the inner diameter of the bore 158 formed in the cam 106.

The top portion 152 of the cam 106 may include a fastener engaging mechanism 159 for engaging a surgical tool to facilitate rotation of the cam 106 from a first position to one or more optional intermediate positions to a second position, as will be described in greater detail below. The fastener engaging mechanism 159 may be any mechanism known in the art including, but not limited to, a screwdriver, a ratchet, a socket, etc. As shown, the fastener engaging mechanism 159 may be a gear-shaped portion 160 sized and configured to engage a corresponding surgical tool such as, for example the drive mechanism 62, previously mentioned.

As previously mentioned, the cam 106 may also include a groove 153, more preferably a circumferential groove that matches the size and contour of the dowel rod 131. In use, the cam 106 may be aligned such that the dowel rod 131 is at least partially inserted through the lateral bore 132 formed in the housing 110 and into the groove 153 formed in the cam 106 so that the cam 106 is prevented from being removed from the housing 110. In addition, as will be readily understood by one of ordinary skill in the art, the incorporation of the groove 153 formed in the cam 106 and the dowel rod 131 inserted through the lateral bore 132 of the housing 110 may act to limit or control the amount of rotational movement of the cam 106 with respect to the housing 110. For example, the groove 153 may extend around only a portion of the cam 106 to permit limited rotation of the cam 106 with respect to the housing 110. Alternatively, the amount of permitted rotation may be limited by the shape of the lobes, preferably the shape of the second lobe 157a, formed on the cam 106 and the interaction of the lobes with the protrusions formed on the collet 108, preferably by the interaction of the second lobe 157a with the second protrusion 177, as will be described in greater detail below. Preferably, the outrigger 105 is sized and configured to permit the cam 106 to rotate less than 360 degrees, such as, for example, 30, 60, 145, 180, 270, etc. Although, as generally known in the art, the cam 106 may be sized and configured to rotate any number of degrees.

The cam 106 may also include a first lobe 157 and a second lobe 157a formed thereon. Preferably, the second lobe 157a may be rotationally offset from the first lobe 157. As shown, preferably the second lobe 157a is formed on the bottom portion 156 of the cam 106 while the first lobe 157 is located in between the second lobe 157a and the top portion 152. For example, when viewed from the bottom, the cam 106 may have two portions with non-circular diameters such that the radius of the cam 106 with respect to the longitudinal axis of the bore 158 is different. In this manner, the cam 106 is in the form of a dual eccentric cam. Alternatively and/or in addition, the cam 106 may include any number of lobes, for example, three, four or more. The lobes may be sized and configured to apply varying forces to the collet 108 so that the longitudinal spinal rod 36 may be clamped with varying degrees of force.

Figure 16:
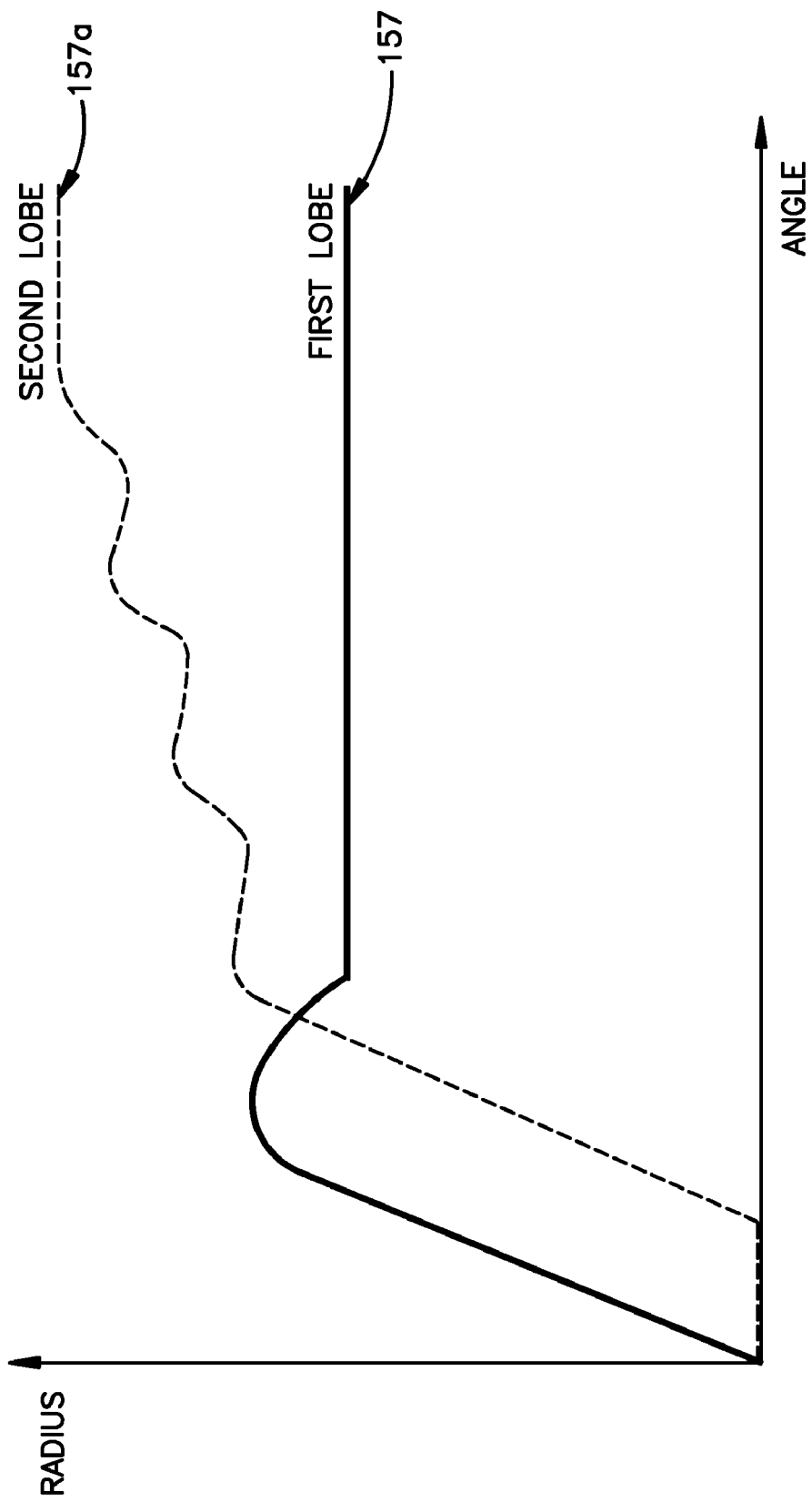
FIG. 16 is a chart depicting an exemplary radius profile for the lobes of a cam that can be used with the outrigger shown in FIG. 7.

As shown, for example in FIG. 16, the first lobe 157 and the second lobe 157a may have different lobe radius profiles. For example, the first lobe 157 may include a single radius profile while the second lobe 157a preferably is formed with a stepped radius profile that incorporates one or more flat surfaces, shown in FIG. 10 as 161a, 161b, 161c, 161d, 161e. The flat surfaces preferably have various radii with respect to the longitudinal axis of the bore 158. It should be understood that the lobe radius profiles shown are but one example and it is envisioned that other lobe radius profiles may be used. Moreover, it should be understood that the stepped lobe profile may include more or less flat surfaces. The first lobe 157 may include a stepped radius profile similar to or different from the second lobe 157a. The second lobe 157a may include a single radius profile similar to or different from the first lobe 157.

Preferably, the radius of the second lobe 157a extends beyond the radius of the first lobe 157, this ensures that the outrigger 105 can be properly secured regardless of the tolerances of all the parts involved. Moreover, incorporation of a stepped radius profile in the second lobe 157a helps to ensure that the outrigger 105 can be secured in various stable positions without the danger of the cam 106 moving out of engagement.

As previously mentioned, the amount of permitted rotation may be limited by the shape of the second lobe 157a formed on the cam 106 and the interaction of the second lobe 157a with the second protrusion 177 formed on the collet 108. For example, as best shown in FIG. 10, if the second lobe 157a is formed with a stepped radius profile, the profile of the second lobe 157a is preferably sized and configured so that, in use, counter-clockwise rotation of the cam 106 may be limited by engagement of one or more of the stepped radii contacting the second protrusion 177. Alternatively and/or in addition, rotating the cam 106 clockwise may be limited by the increasing radius of the second lobe 157a contacting the second protrusion 177.

As will be described in greater detail below, rotation of the cam 106 preferably causes the first lobe 157 formed on the cam 106 to contact and/or engage a first protrusion 179 formed on the collet 108. At this point, preferably the second lobe 157a formed on the cam 106 does not contact and/or engage a second protrusion 177 formed on the collet 108. As rotation of the cam 106 continues, the first lobe 157 formed on the cam 106 preferably disassociates and/or disengages from the first protrusion 179 formed on the collet 108. At this point, however, the second lobe 157a formed on the cam 106 preferably contacts and/or engages the second protrusion 177 formed on the collet 108.

As shown in FIG. 9, the collet 108 may include a first side 165, a second side 166, a third side 167, a fourth side 168, a top side 169, a bottom side 170 and a passage 174 extending from the first side 165 to the second side 166 of the collet 108. The passage 174 is preferably sized and configured to receive at least some portion of the longitudinal spinal rod 36, and more preferably may be sized and configured so that once the collet 108 is inserted into the housing 110 via the third opening 127, the passage 174 formed in the collet 106 may be aligned with the second throughbore 125 formed in the housing 110 so that the longitudinal spinal rod 36 may be received and/or passed through the housing 110. As shown, the first and second sides 165, 166 may include a tapered depression 176 formed thereon, the tapered depression 176 facilitating easier insertion of the spinal rod 36 through the collet 108. Angular movement of the longitudinal spinal rod 36 with respect to the housing 110 may be enabled through articulation of the outer, preferably cylindrical, surface of the collet 108 contacting the inner surface of the second throughbore 125 formed in the housing 110. Alternatively, as previously mentioned, the spinal rod 36 and collet 108 may be formed as one piece.

As shown, one of the third or fourth sides 167, 168 (shown as the fourth side 168) may include a first surface and a second surface for contacting the cam 106, preferably a first protrusion 179 and a second protrusion 177 for contacting the first lobe 157 and the second lobe 157a, respectively, while the other of the third or fourth sides 167, 168 (shown as the third side 167) may include a roughened surface 172 for contacting the roughened surface 142 formed on the end member 140. More preferably, as shown, the collet 108 may include a first projection 179 for contacting the first lobe 157 formed on the cam 106 such that rotation of the cam 106 preferably causes the first lobe 157 to contact and/or engage the first protrusion 179 formed on the collet 108, which in turn preferably causes the roughened surface 172 formed on the collet 108 to contact and/or engage the roughened surface 142 formed on the end member 140. Engagement of the roughened surface 172 formed on the collet 108 with the roughened surface 142 formed on the end member 140 preferably causes the collet 108 to become rotationally fixed with respect to the end member 140 which in turn preferably causes the articulation of the longitudinal spinal rod 36 to be fixed with respect to the housing 110. Moreover, preferably the collet 108 may include a second projection 177 for contacting the second lobe 157a formed on the cam 106 such that further rotation of the cam 106 preferably causes the second lobe 157a to contact and/or engage the second protrusion 177 formed on the collet 108, which in turn preferably causes the collet 108 to compress around the longitudinal spinal rod 36 which in turn preferably causes the position of the spinal rod 36 and the bone anchor 22 to be fixed with respect to the housing 110, as will be described in greater detail below.

Moreover, as shown, the collet 108 may include a slot 178 formed therein, the slot 178 preferably extending from the first side 165 to the second side 166. The slot 178 also preferably may be in communication with the passage 174 so that, as generally understood by one of ordinary skill in the art, the collet 108 may be compressible. In its natural state, the collet 108 is preferably sized and configured in a first configuration such that the longitudinal spinal rod 36 may move (e.g., translate, rotate, articulate, etc.) within the passage 174. Thereafter, application of a force, for example by rotation of the cam 106, preferably causes the collet 108 to move to a second configuration wherein the longitudinal spinal rod 36 is substantially prevented from articulating with respect to the housing 110. Thereafter, application of another and/or an additional force, for example by further rotation of the cam 106, preferably causes the collet 108 to move to a second configuration wherein the longitudinal spinal rod 36 is substantially prevented from any movement (e.g., translation, rotation, articulation, etc.) within the passage 74. In this manner, initial rotation of the cam 106 from the cam's first position to the cam's intermediate position preferably causes the first lobe 157 to contact and/or engage the collet 108, which in turn preferably causes the roughened surface 172 formed on the collet 108 to engage the roughened surface 142 formed on the end member 140, however, engagement of the first lobe 157 with the first protrusion 179 preferably does not apply a force to cause the collet 108 to compress around the spinal rod 36. Further rotation of the cam 106 from the cam's intermediate position to the cam's second position preferably causes the second lobe 157a to contact and/or engage the collet 108, which in turn applies a force to the collet 108, causing the collet 108 to compress around some portion of the spinal rod 36, thereby fixing the position (e.g., translation) of the spinal rod 36 with respect to the housing 110. As shown, the passage 174 may include a threaded, serrated or roughened surface 180 to further help prevent movement of the longitudinal spinal rod 36 when the collet 108 is in the second configuration.

In use, the outrigger 105 may be pre-assembled by the manufacturer and/or surgeon so that the cam 106 and the collet 108 are preferably secured within the housing 110. Next, the longitudinal spinal rod 36 may be passed through the second throughbore 125 formed in the housing 110 and the passage 174 formed in the collet 108. The outrigger 105 may then be connected to the bone anchors 22 that may have been previously secured to a patient's bone, for example, a vertebra. The shaft portion 24 of the bone anchor 22 may be received by the first throughbore 124 formed in the housing 110 and by the bore 158 of the cam 106. Alternatively, as will be generally understood by one of ordinary skill in the art, the outrigger 105 may be secured to the bone anchor 22 prior to the bone anchors 22 being secured to the patient's bone. Moreover, the outrigger 105 and bone anchors 22 may be secured to the patient's bone prior to the spinal rod 36 being inserted into the second throughbore 125 of the housing 110 and the passage 174 in the collet 108.

Figure 11:
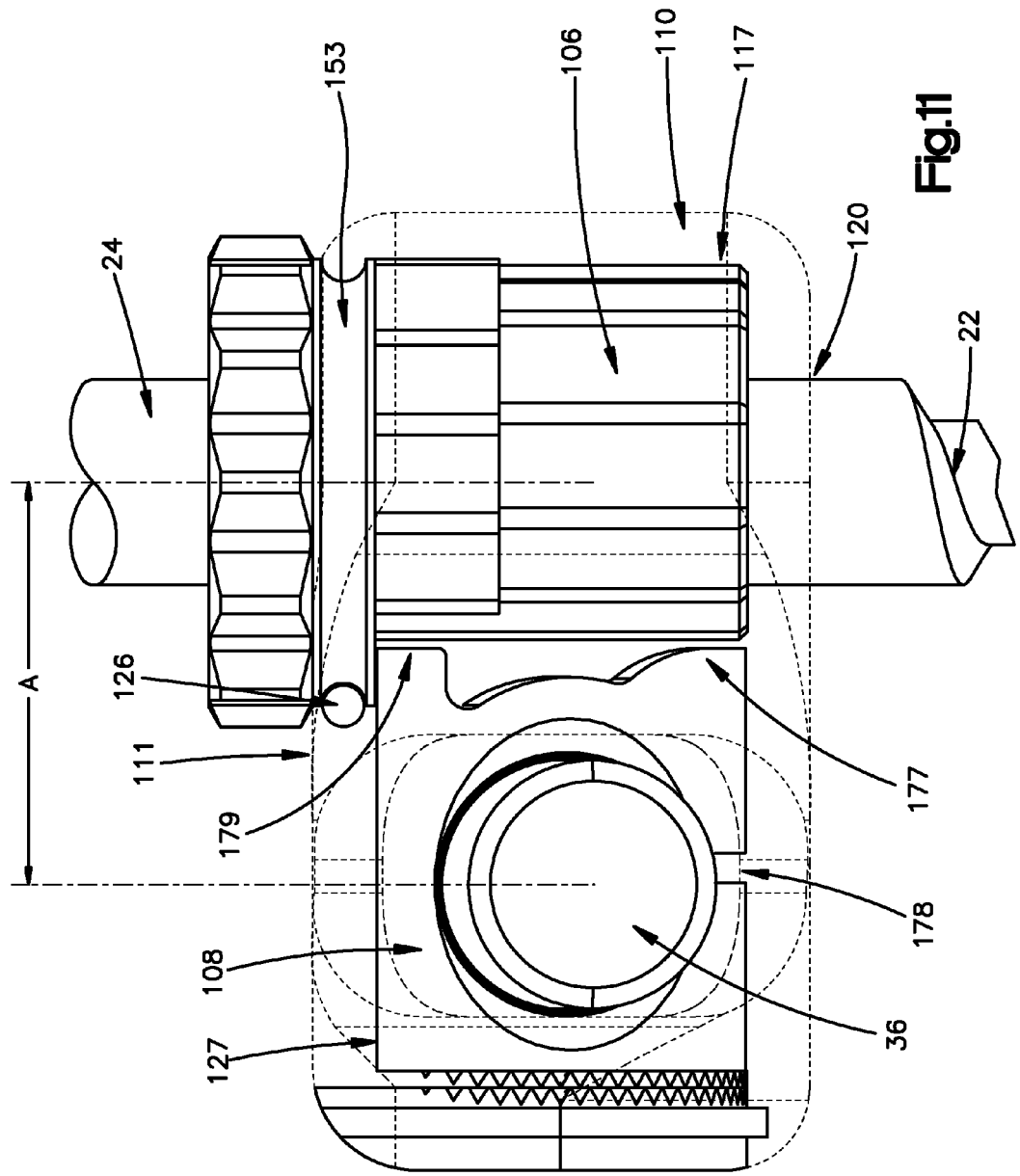
FIG. 11 is a side view of the outrigger shown in FIG. 7 in the first position, with parts in phantom to show the internal components.
Figure 12:
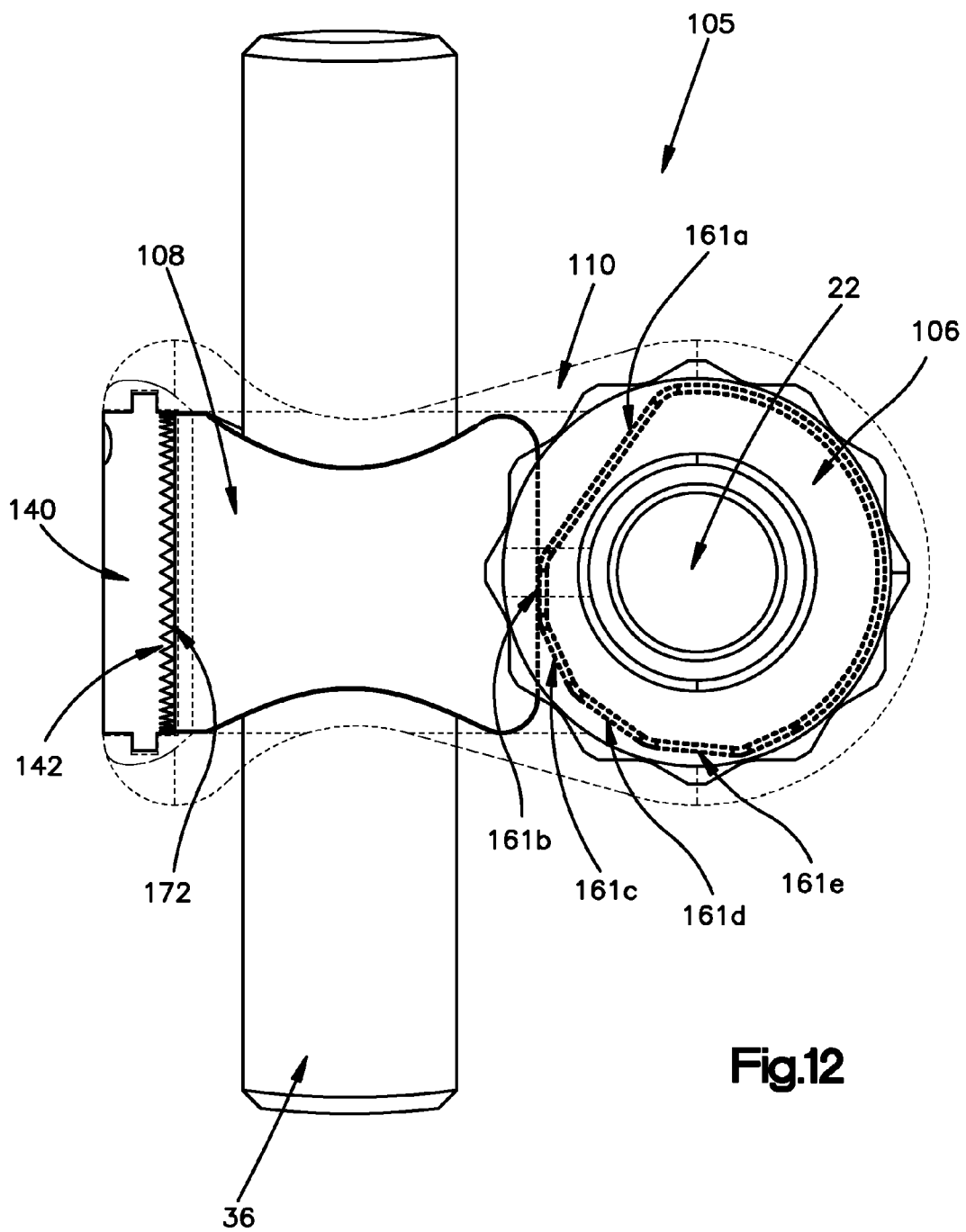
FIG. 12 is a top view of the outrigger shown in FIG. 7 in an intermediate position, with parts in phantom to show the internal components.
Figure 13:
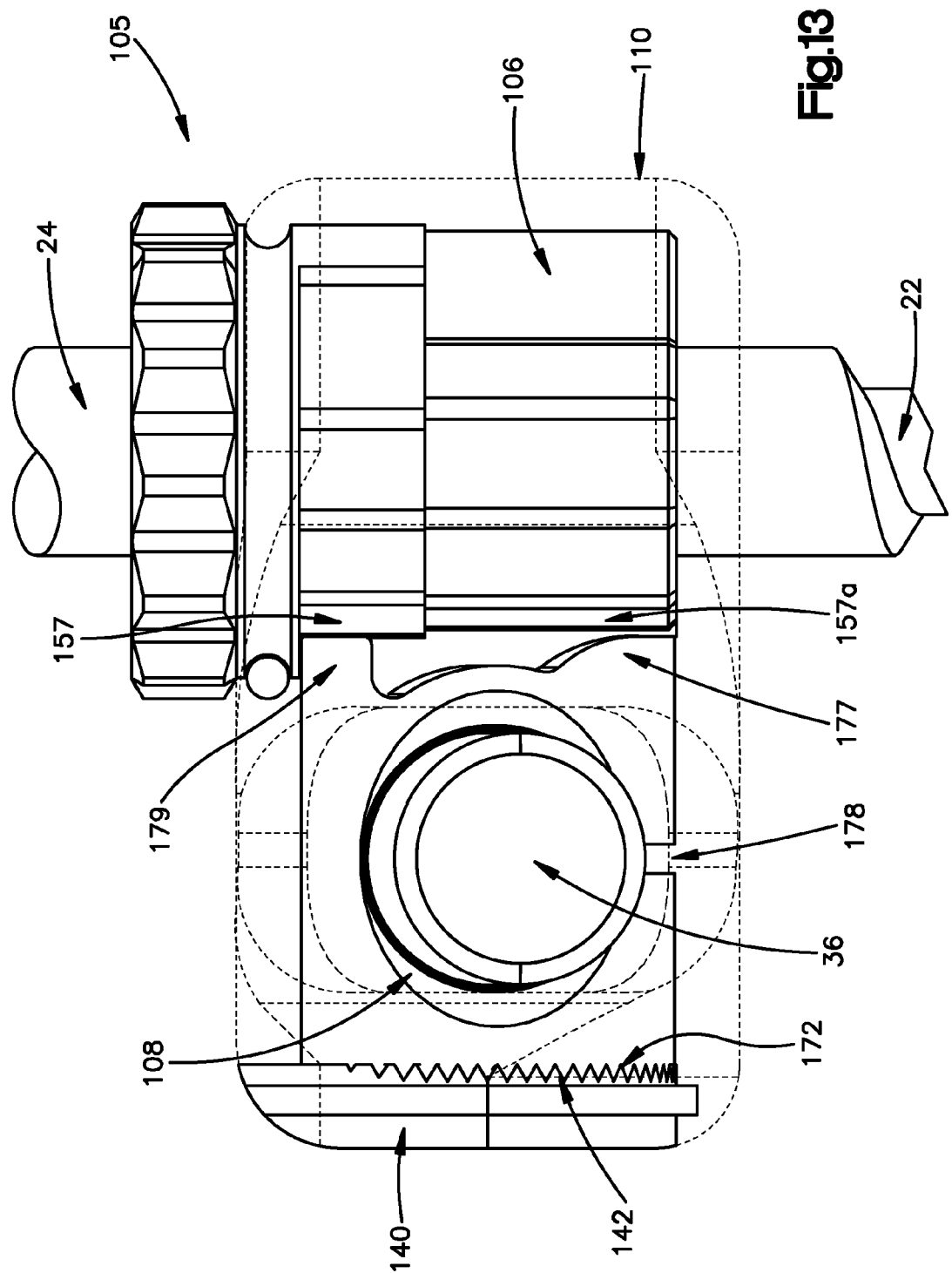
FIG. 13 is a side view of the outrigger shown in FIG. 7 in the intermediate position, with parts in phantom to show the internal components.
Figure 14:
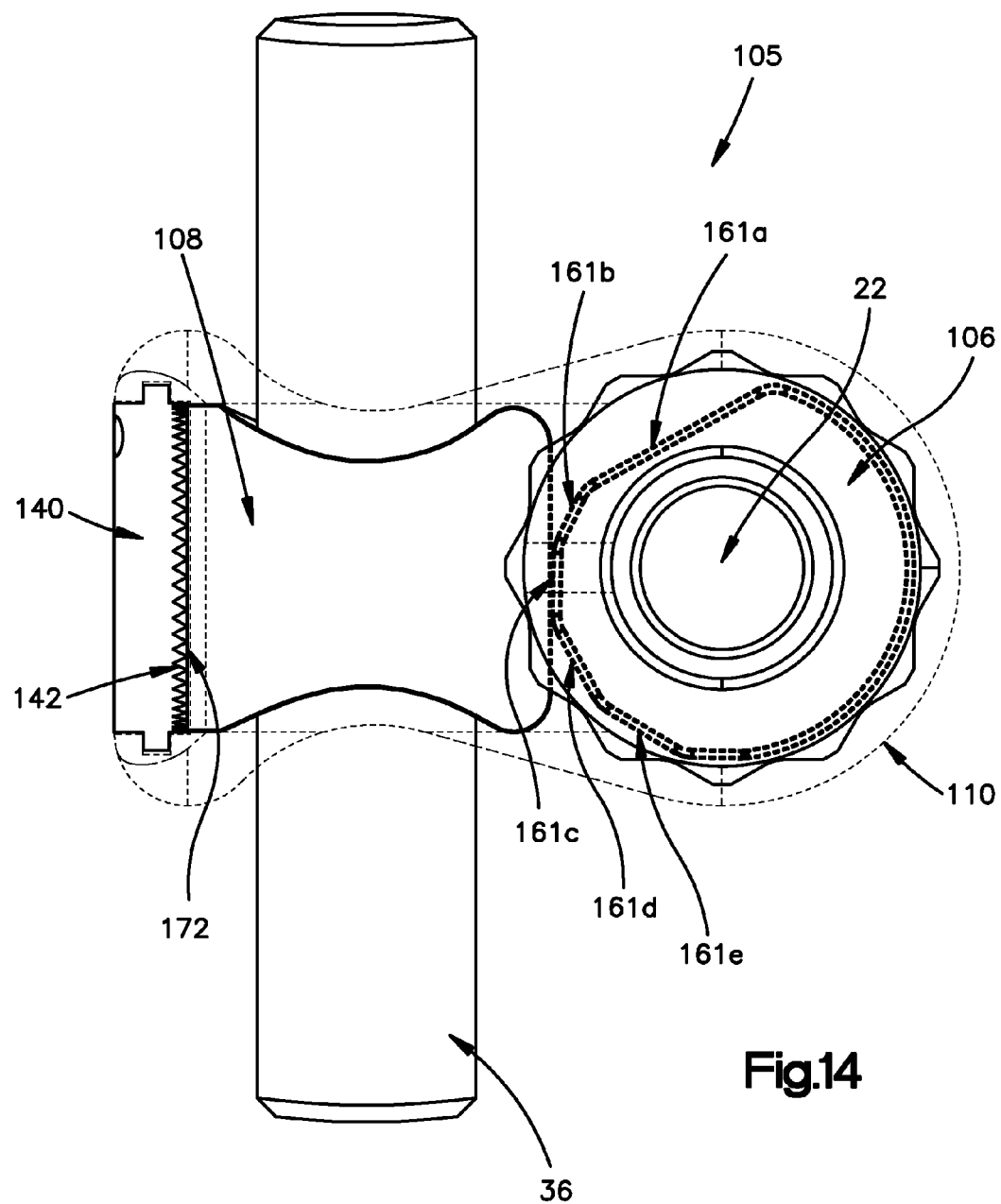
FIG. 14 is a top view of the outrigger shown in FIG. 7 in the second position, with parts in phantom to show the internal components.
Figure 15:
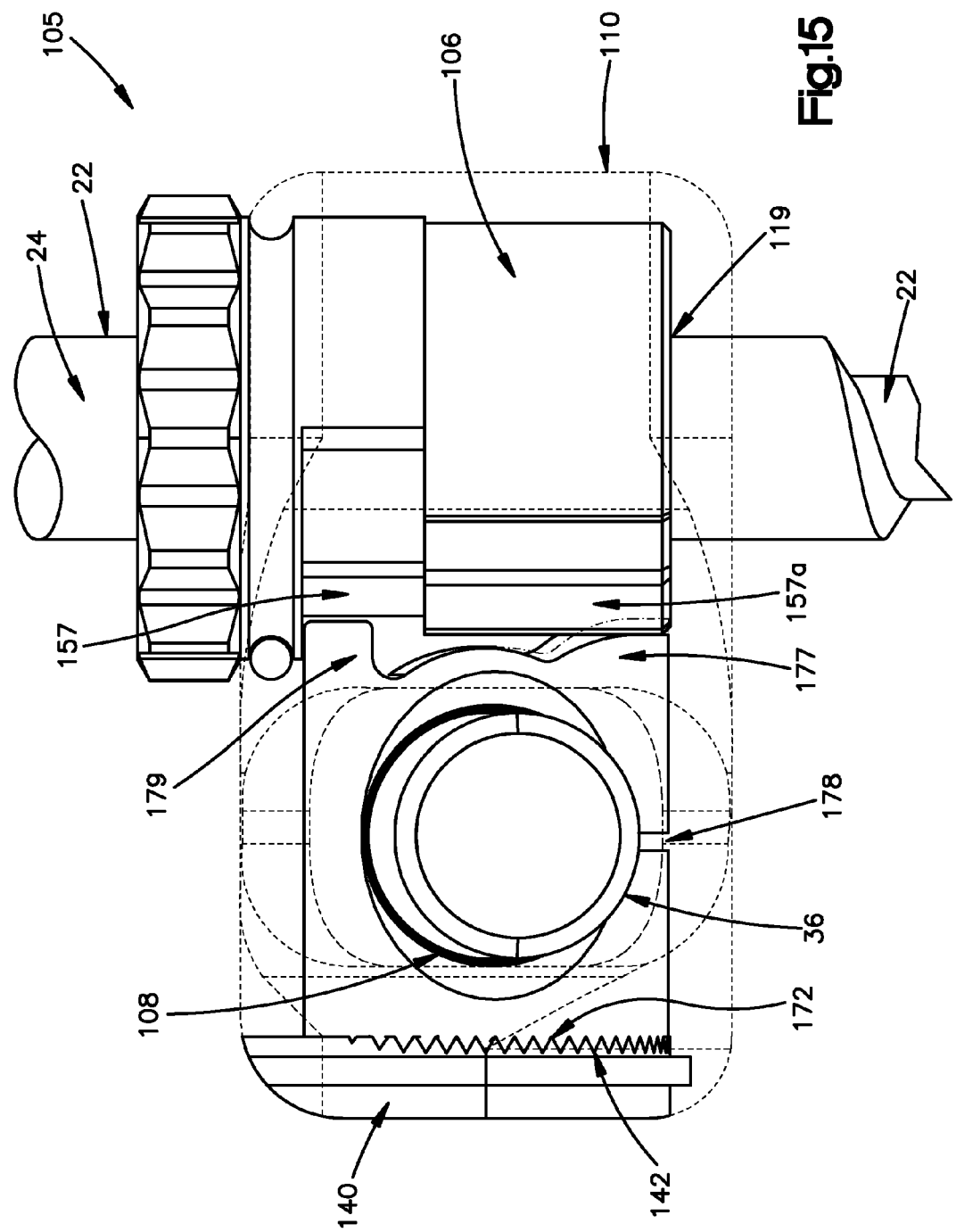
FIG. 15 is a side view of the outrigger shown in FIG. 7 in the second position, with parts in phantom to show the internal components.

As best shown in FIGS. 10 and 11, the cam 106 is received in the housing 110 in a first position whereby the cam 106 preferably does not contact and/or engage the collet 108 so that the collet 108 may be in the first configuration and the collet 108 preferably does not contact and/or engage the end member 140. In this position, the longitudinal spinal rod 36 may freely move with respect to the housing 110 and the bone anchor 22 may freely move with respect to the housing 110. Once the desired position has been achieved, the surgeon may use a surgical tool, such as the drive mechanism 62 previously mentioned, to engage the fastener engaging mechanism 159 formed on the top portion 152 of the cam 106. Thereafter, as best shown in FIGS. 12 and 13, rotation of the surgical tool preferably causes the cam 106 to rotate to an intermediate position wherein the cam 106 partially contacts and/or engages the collet 108, which in turn, preferably causes the collet 108 to contact and/or engage the end member 140. At this point however preferably no force is applied to compress the collet 108 around the spinal rod 36. In this manner, the collet 108 may become rotationally secured with respect to the end member 140, yet still allow the longitudinal spinal rod 36 to translate with respect to the housing 110. Thereafter, as best shown in FIGS. 14 and 15, further rotation of the surgical tool preferably causes the cam 106 to further rotate, which in turn preferably causes the cam 106 to contact and/or engage the collet 108. This, in turn, preferably causes the collet 108 to move and/or transition from its first configuration, wherein the spinal rod 36 is free to move with respect to the house 110, to its second configuration, wherein the spinal rod 36 is substantially prevented from moving with respect to the housing 110. In the second configuration, the collet 108 is preferably compressed around some portion of the spinal rod 36 thereby preventing translational movement of the spinal rod 36.

More specifically, preferably, rotation of the surgical tool causes the cam 8 to rotate, which in turn preferably causes the first lobe 157 formed on the cam 108 to contact and/or engage the first protrusion 179 formed on the collet 108, which in turn preferably causes the roughened surface 172 formed on the collet 108 to contact and/or engage the roughened surface 142 formed on the end member 140. At this point, preferably no force to compress the collet 108 has been applied. In this manner, the collet 108 may become rotationally secure with respect to the end member 140, yet still allow the longitudinal spinal rod 36 to translate with respect to the housing 110. Further rotation of the cam 106 may cause the second lobe 157*a* formed on the cam 106 to contact and/or engage the second protrusion 177 formed on the collet 108. This, in turn, may cause the collet 108 to move and/or transition to its second configuration, wherein the spinal rod 36 is substantially prevented from moving (e.g. translation) with respect to the housing 110.

Additionally, similar to the outrigger 5 described above, the application of force to the collet 108 by the second lobe 157*a* formed on the cam 106 may result in a force of equal magnitude and opposite direction being applied to the cam 106, and hence to the bone anchor 22. In this manner, at least a portion of the shaft portion 24 of the bone anchor 22 may be biased against the housing 110, for example, in the area 119 of the housing 110 below the cam 106 thereby securing the bone anchor 22 with respect to the housing 110.

As will be appreciated by those skilled in the art, any or all of the components described herein such as, for example, the rods, outrigger, housing, pedicle screws, etc. may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same device may be provided in different shapes and/or sizes (e.g., multiple rods, outriggers, housings and/or pedicle screws of different sizes).

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. An outrigger for securing a longitudinal spinal rod with respect to a bone anchor, the outrigger comprising:
   a housing having a first throughbore sized and configured to receive at least a portion of the bone anchor, a second throughbore sized and configured to receive at least a portion of the spinal rod, and an opening formed in a side thereof for receiving a collet;
   a cam having a bore sized and configured to at least partially surround at least a portion of the bone anchor, the cam being at least partially disposed within the first throughbore and rotatable from a first position to a second position to secure the spinal rod to the housing;
   the collet having a passage sized and configured to surround at least a portion of the spinal rod, the collet being at least partially disposed within the second throughbore; and
   an end member securable to the housing for closing the opening of the housing;
   wherein the cam is moveable from a first position to a second position such that, in the first position the spinal rod and bone anchor are free to move with respect to the housing, and in the second position the spinal rod and the bone anchor are secured with respect to the housing.

2. The outrigger of claim 1, wherein the cam is moveable to an intermediate position wherein in the intermediate position the spinal rod is free to translate with respect to the housing but is prevented from articulating with respect thereto.

3. The outrigger of claim 2, wherein the cam includes a first lobe and a second lobe, wherein movement of the cam from the first position to the intermediate position causes the first lobe to move to a first lobe position where the first lobe contacts the collet.

4. The outrigger of claim 3, wherein movement of the cam from the intermediate position to the second position causes the second lobe to move to a second lobe position where the second lobe contacts the collet.

5. The outrigger of claim 4, wherein the collet includes a first protrusion and a second protrusion, the first protrusion being sized and configured to contact the first lobe when the cam is rotated to the intermediate position and the second protrusion being sized and configured to contact the second lobe when the cam is rotated to the second position.

6. The outrigger of claim 5, wherein movement of the cam from the first position to the intermediate position causes the first lobe to contact the first protrusion which, in turn, causes the collet to engage an end member and wherein movement of the cam from the intermediate position to the second position causes the second lobe to contact the second protrusion which, in turn, causes the collet to compress around at least a portion of the spinal rod.

7. The outrigger of claim 1, wherein the collet is moveable between a first configuration and a second configuration, the collet being compressed in the second configuration.

8. The outrigger of claim 7, wherein movement of the cam from the first position to the second position causes the cam to contact the collet, which in turn causes the collet to move from the first configuration to the second configuration thereby fixing the position of the spinal rod with respect to the housing.

9. The outrigger of claim 1, wherein the end member includes a roughened surface for engaging a roughened surface formed on the collet when the cam is moved from the first position to the second position.

10. The outrigger of claim 9, wherein the lobe contacting the protrusion causes the roughened surface formed on the collet to engage the roughened surface formed on the end member.

11. The outrigger of claim 1, wherein the outrigger includes a key mechanism, the key mechanism limiting the orientation of the cam with respect to the housing.

12. The outrigger of claim 11, wherein the key mechanism includes a plate member having an opening formed therein, a pin and a bore formed in the housing, the bore and the opening being sized and configured to receive the pin.

13. The outrigger of claim 1, wherein movement of the cam to the second position causes the cam to contact the collet, which in turn causes the collet to compress around the spinal rod, thereby fixing the position of the spinal rod with respect to the housing.

14. The outrigger of claim 1, wherein the collet includes a slot formed therein, the slot extending from a first side to a second side thereof, the slot being in communication with the passage.

15. The outrigger of claim 1, wherein the cam includes a lobe formed thereon and the collet includes a protrusion formed thereon, the lobe being sized and configured to contact the protrusion when the cam is moved from the first position to the second position.

16. The outrigger of claim 1, wherein the end member includes a roughened surface for engaging a roughened surface formed on the collet.

17. The outrigger of claim 1, wherein the cam moves from the first position to the second position upon rotation of the cam.

18. The outrigger of claim 1, wherein movement of the cam from the first position to the second position causes the bone anchor to contact the housing thereby fixing the position of the bone anchor with respect to the housing.

19. An outrigger for securing a longitudinal spinal rod with respect to a bone anchor, the outrigger comprising:

a housing having a first throughbore sized and configured to receive at least a portion of the bone anchor and a second throughbore sized and configured to receive at least a portion of the spinal rod;

a cam having a bore sized and configured to at least partially surround at least a portion of the bone anchor, the cam being at least partially disposed within the first throughbore and rotatable from a first position to a second position to secure the spinal rod to the housing;

a collet having a passage sized and configured to surround at least a portion of the spinal rod, the collet being at least partially disposed within the second throughbore; and a key mechanism including a plate member having an opening formed therein, a pin and a bore formed in the housing, the bore and the opening being sized and configured to receive the pin;

wherein the key mechanism limits the orientation of the cam with respect to the housing;

wherein the cam is moveable from a first position to a second position such that, in the first position the spinal rod and the bone anchor are free to move with respect to the housing, and in the second position the spinal rod and bone anchor are free to move with respect to the housing, and in the second position the spinal rod and the bone anchor are secured with respect to the housing.

20. An outrigger for securing a longitudinal spinal rod with respect to a bone anchor, the outrigger comprising:

a housing having a first throughbore sized and configured to receive at least a portion of the bone anchor, a second throughbore sized and configured to receive at least a portion of the spinal rod;

a cam having a bore sized and configured to at least partially surround at least a portion of the bone anchor, the cam being at least partially disposed within the first throughbore and rotatable from a first position to a second position to secure the spinal rod to the housing, the cam including a first lobe and a second lobe; and a collet having a passage sized and configured to surround at least a portion of the spinal rod, the collet being at least partially disposed within the throughbore;

wherein the cam is moveable from a first position to a second position such that, in the first position the spinal rod and bone anchor are free to move with respect to the housing, and in the second position the spinal rod and the bone anchor are secured with respect to the housing;

wherein the cam is moveable to an intermediate position wherein in the intermediate position the spinal rod is free to translate with respect to the housing but is prevented from articulating with respect thereto;

wherein movement of the cam from the first position to the intermediate position causes the first lobe to move to a first lobe position where the first lobe contacts the collet;

wherein movement of the cam from the intermediate position to the second position causes the second lobe to move to a second lobe position where the second lobe contacts the collet;

wherein the collet includes a first protrusion and a second protrusion, the first protrusion being sized and configured to contact the first lobe when the cam is rotated to the intermediate position and the second protrusion being sized and configured to contact the second lobe when the cam is rotated to the second position.

* * * * *